(12) United States Patent
Madhavamenon et al.

(10) Patent No.: US 10,610,562 B2
(45) Date of Patent: Apr. 7, 2020

(54) INSTANT WATER SOLUBLE BIOACTIVE DIETARY PHYTONUTRIENTS COMPOSITION OF SPICE/HERB EXTRACTS AND A PROCESS FOR ITS PREPARATION

(71) Applicant: AKAY FLAVOURS & AROMATICS PVT. LTD, Kerala (IN)

(72) Inventors: Krishnakumar Illathu Madhavamenon, Kerala (IN); Balu Paulose Maliakel, Kerala (IN)

(73) Assignee: AKAY FLAVOURS & AROMATICS PVT. LTD, Kerala (IN)

( * ) Notice: Subject to any disclaimer, the term of this patent is extended or adjusted under 35 U.S.C. 154(b) by 85 days.

(21) Appl. No.: 14/735,169

(22) Filed: Jun. 10, 2015

(65) Prior Publication Data
US 2015/0352173 A1 Dec. 10, 2015

(30) Foreign Application Priority Data
Jun. 10, 2014 (IN) .......................... 2833/CHE/2014

(51) Int. Cl.
| | |
|---|---|
| *A61K 36/9068* | (2006.01) |
| *A23L 2/52* | (2006.01) |
| *A61K 31/192* | (2006.01) |
| *A61K 36/23* | (2006.01) |
| *A61K 36/61* | (2006.01) |
| *A61K 36/9064* | (2006.01) |
| *A61K 36/54* | (2006.01) |
| *A23L 33/105* | (2016.01) |
| *A23L 19/18* | (2016.01) |

(52) U.S. Cl.
CPC ............ *A61K 36/9068* (2013.01); *A23L 2/52* (2013.01); *A23L 19/18* (2016.08); *A23L 33/105* (2016.08); *A61K 31/192* (2013.01); *A61K 36/23* (2013.01); *A61K 36/54* (2013.01); *A61K 36/61* (2013.01); *A61K 36/9064* (2013.01); *A61K 2236/00* (2013.01)

(58) Field of Classification Search
None
See application file for complete search history.

(56) References Cited

U.S. PATENT DOCUMENTS

| | | |
|---|---|---|
| 5,525,260 A | 6/1996 | Aeschbach et al. |
| 5,985,352 A | 11/1999 | Todd |
| 2004/0161524 A1* | 8/2004 | Sakai ................... A61K 36/185 426/655 |
| 2010/0021578 A1 | 1/2010 | Coleman et al. |

FOREIGN PATENT DOCUMENTS

| | | | |
|---|---|---|---|
| CN | 102302732 A | * | 1/2012 |
| CN | 102600423 A | * | 7/2012 |
| WO | 2007130666 A2 | | 11/2007 |
| WO | 2007130666 A3 | | 11/2007 |
| WO | 2013049540 A2 | | 4/2013 |
| WO | 2013049540 A3 | | 4/2013 |
| WO | 2013057520 A1 | | 4/2013 |

OTHER PUBLICATIONS

Rita Aquino et al, "Phenolic Constituents and Antioxidant Activity of an Extract of Anthurium Versicolor Leaves"—1019-1023—American Chemical Society and American Socirty of Parmacognosy—Published on Web Jul. 18, 2001.
Iris F.F.Benzle and J.J.Strain—"The Ferric Reducing Ability of Plasma (FRAP) as a Measure of "Antioxidant Power": The FRAP Assay"—Analytical Biochemistry 239, 70-76 (1996) Article No. 0292.
Bharat B. Aggarwal—"Targeting Inflammation-Induced Obesity and Metabolic Diseases by Curcumin and Other Nutraceuticals"—Review in Advance first posted online on Apr. 26, 2010.
Christine M Kaefer and John A, Milner—"The Role of Herbs and Spices in Cancer Prevention" NIH Public Access—Author Manuscript J Nutr Biochem. Author manuscript; availbale in PMC Nov. 2, 2009.
Elizabeth Kunchandy and M.N.A. Rao "Oxygen Radical Scavenging Activity of Curcumin" International Journal of Pharmaceutics 58 (1990) 237-240.
Hannah R. Vasanthi and R.P. Parameswari "Indian Spices for Healthy Heart—An Overview"—Current Cardiology Reviews, 2010, 6, 274-279.
Jenny Epstein, Ian R. Sanderson and Thomas T. Macdonald—"Curcumin as a Therapeutic Agent: The Evidence From In Vitro, Animal and Human Studies" British Journal of Nutrition (2010) 103, 1545-1557.
Kalyan Reddy Manda, Craig Adams, Nuran Ercal "Biologically Improtant Thiols in Aqueous Extracts of Spices and Evaluation of Their In Vitro Antioxidant Properties" Food Chemistry 118 (2010) 589-593—journal homepage: www.elsevier.com/locate/foodchem.
Joe M. McCord and Irwin Fridovich Superoxide Dismutase—An Enzymic Function for Erythrocuprein (Hemocuprein)—The Journal of Biological Chemistry, vol. 244, No. 22, Issue of Nov. 5, pp. 6049-6055, 1969.
Monica H Carlsen et al "The Total Antioxidant Content of More Than 3100 Foods, Beverages, Spices, Herbs and Supplements Used Worldwide" Carlsen et al. Nutrition Journal 2010, http://www.nutritionj.com/content/9/1/3.
Maria S. Moron et al. "Levels of Glutathione, Glutathione Reductase and Glutathione S-transferase Activities in Rat Lung and Liver" Biochimica et Biophysica Acta, 582 (1979) 67-78. Elsevier/North-Holland Biomedical Press.

(Continued)

*Primary Examiner* — Amy L Clark
(74) *Attorney, Agent, or Firm* — Mark M. Friedman

(57) ABSTRACT

The present invention relates to a method for the preparation of the instant water soluble, stable, phytonutrient rich spice/herb extracts exhibiting significant antioxidant and other bioactivities, in a ready to use form and a composition for beverage and food applications to deliver physiologically relevant amounts of phytonutrients per serving without taste or aroma issue and in organic quality. The composition derived in the present invention include the bioactive phytonutrient molecules along with its natural counter parts comprising mainly proteins, carbohydrates and dietary fibre of the spice and/or herb.

17 Claims, 8 Drawing Sheets

(56) References Cited

OTHER PUBLICATIONS

Hiroshi Ohkawa et al. "Assay for Lipid Peroxides in Animal Tissues by Thiobarbituric Acid Reaction" Analytical Biochemisrty 95, 351-358 (1979).
K. Vali Pasha and B. Sadasivudu "Intracellular Content of Thiol Compounds, Thiobarbituric Acid Reactive Substances and Gamma-Glutamyl Transpeptidase in Rat Brain Duing Anoxia" Neuroscience letter, 46, (1984) 209-214 Elsevier Scientific Publishers Ireland Ltd.
Ramaswamy Kannappan et al. "Neuroprotection by Spice-Derived Nutraceuticals: You Are What You Eat!" NIH Public Access—Author Manuscript—Published in Final Edited Form as Mol Neurobiol, Oct. 2011; 44(2); 142-159, doi: 10.1007/s12035-011-8168-2.
Annie Shirwaikar, Kirti S Prabhu & I S R Punitha "In Vitro Antioxidant Studies of Sphaeranthus Indicus (LINN)"—Indian Journal of Experimental Biology—vol. 44 Dec. 2006, pp. 993-996.
Xianli Wu et al "Lipophilic and Hydrophilic Antioxidant Capacities of Common Foods in the United States" J. Agric. Food Chem 2004, 52, 4026-4037.

\* cited by examiner

FIG 1: Polyphenol content of various de-flavoured spice extracts.

| Spices | Polyphenol content (Gallic acid equivalent) | | | | |
|---|---|---|---|---|---|
| | Cumin | Coriander | Clove | Cinnamon | Cardamom |
| Ethanol/water Extraction | 7.25% | 4.5% | 33.25% | 30.2% | 3.3% |
| Acetone/water Extraction | 8.2% | 4.8% | 37.3% | 33.4% | 3.6% |
| Deoiled spices with ethanol/water | 6.8% | 3.8% | 29% | 24.3% | 2.7% |
| Deoiled spices with acetone/water | 7.2% | 4.1% | 32.2% | 29.6% | 3.2% |
| Deoiled spices with water extraction | 5.25% | 2.7% | 22.3% | 20.5% | 2.6% |
| water extraction | 5.15% | 3.3% | 26.4% | 22% | 2.9% |

FIG 2: *In vitro* antioxidant effects of water-soluble spice phytonutrient extracts

| | SOD (µg/ml) | HYDROXYL (µg/ml) | LIPID PEROXIDE (µg/ml) | CAP – e Test (mg Gallic acid) | ORAC (µmol TE/g) |
|---|---|---|---|---|---|
| CUMIN | 9.33 | 275 | 99 | 71 | 4500 |
| GINGER | 30.6 | 159 | 102 | 63 | 5600 |
| CORIANDER | 17.6 | 296 | 125 | 76 | 3800 |
| CLOVE | 12.5 | 185 | 75 | 85 | 9200 |
| VIT C | 1900 | 1550 | 375 | ------ | ----- |

FIG 3: Free radical scavenging activity of water-soluble spice phytonutrient extracts

| | DPPH (µg/mL) | ABTS (µg/mL) | FRAP (µmol/L of $FeSO_4.7H_2O$) |
|---|---|---|---|
| CUMIN | 20.25 | 13.37 | 637.5 |
| GINGER | 25 | 28 | 712.5 |
| CORIANDER | 45 | 14.75 | 512.5 |
| CLOVE | 6 | 12.35 | 635.25 |
| VIT C | 14 | 2.25 | ------ |

FIG 4: Effect of de-flavoured cumin extract incorporated potato chips on the antioxidant activity.
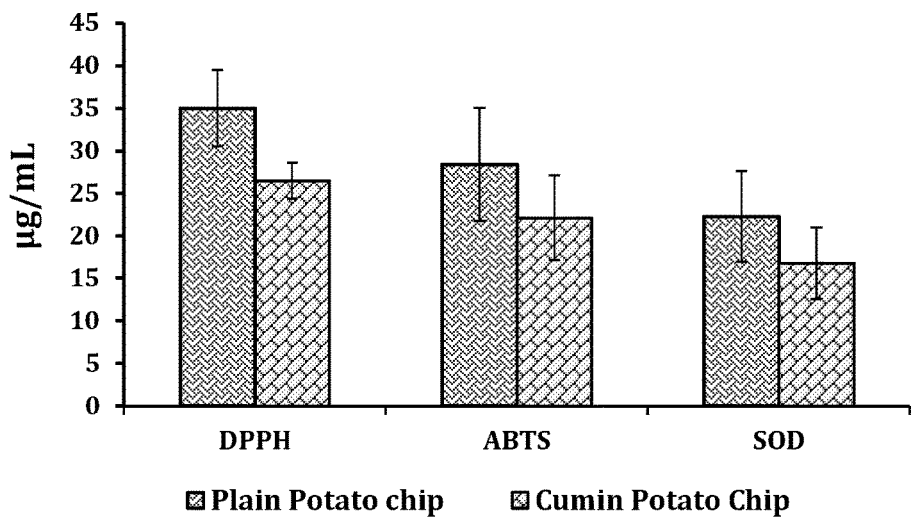
FIG 5: Evaluation of *In vivo* anti-inflammatory potential of water soluble, de-flavored Clove extract
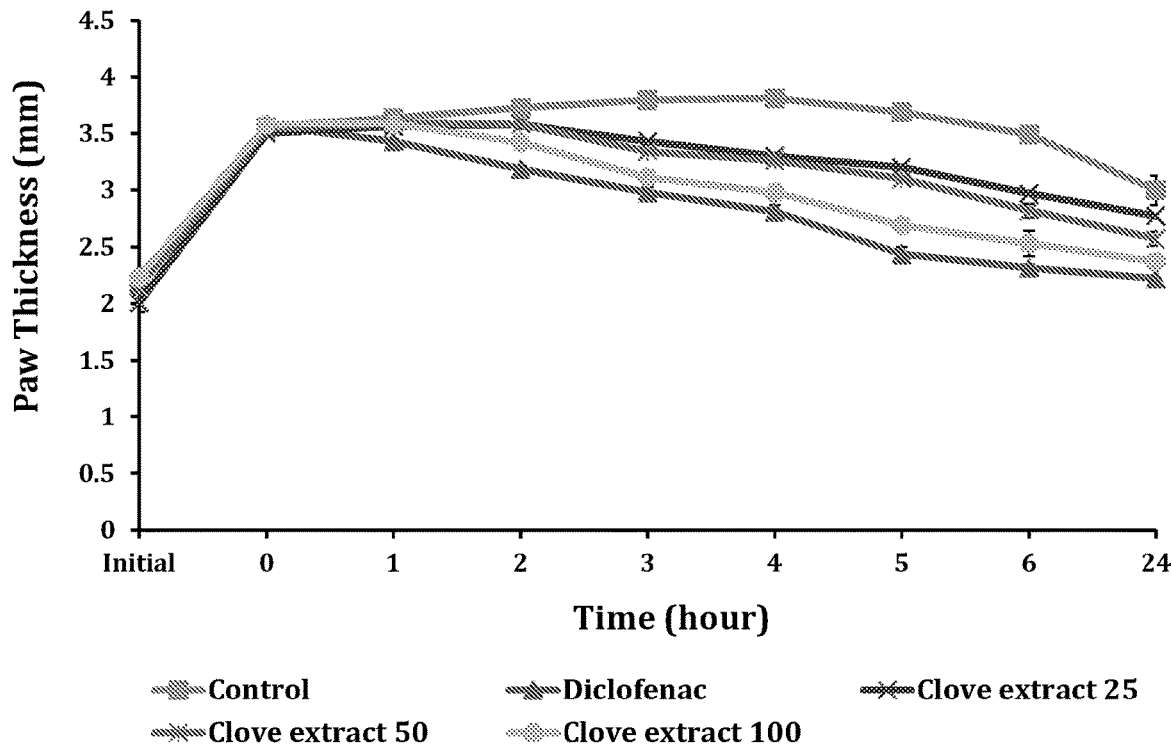

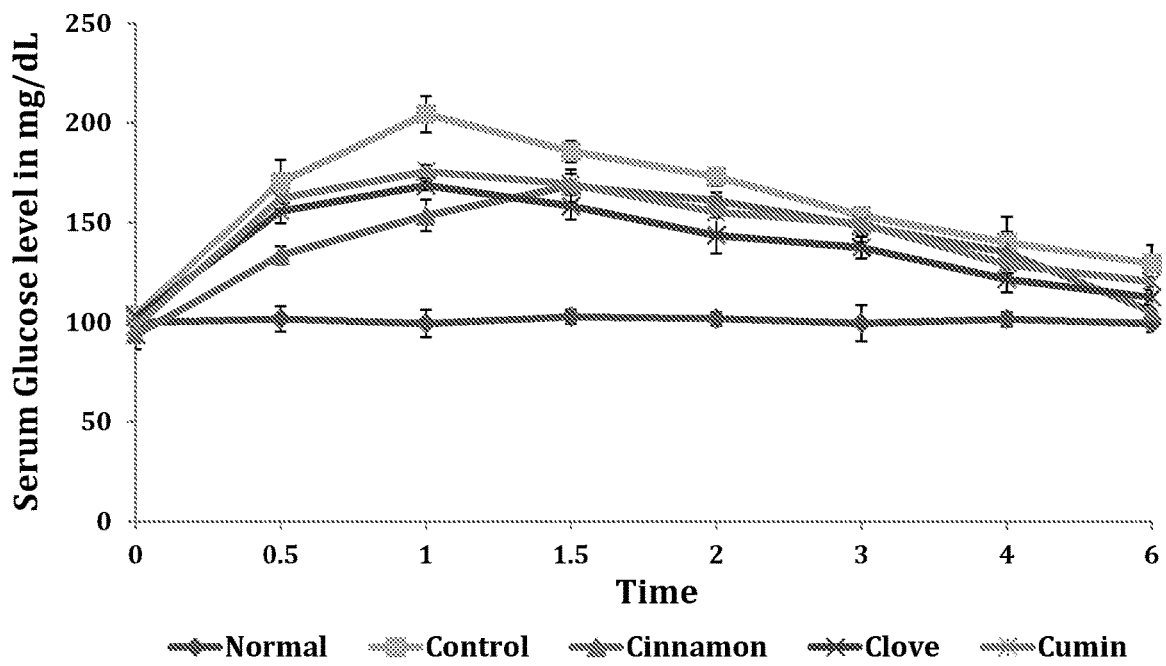
FIG 6: Antidiabetic activity of spice extracts (Cinnamon, Clove & Cumin) by glucose tolerance test
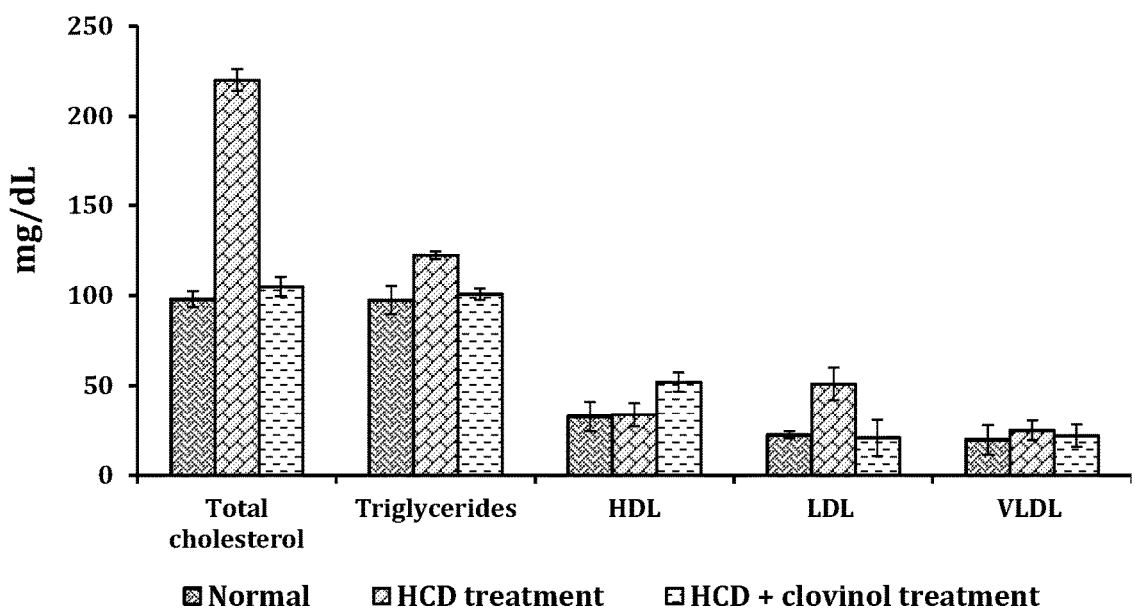
FIG 7: Hypolipidemic activity of clove extract in fat diet induced obese models FIG 8: (A, B & C): Effect of water soluble and deflavoured clove extract impregnated food consumption on oxidative stress of healthy human volunteers.
(Fig 8A)
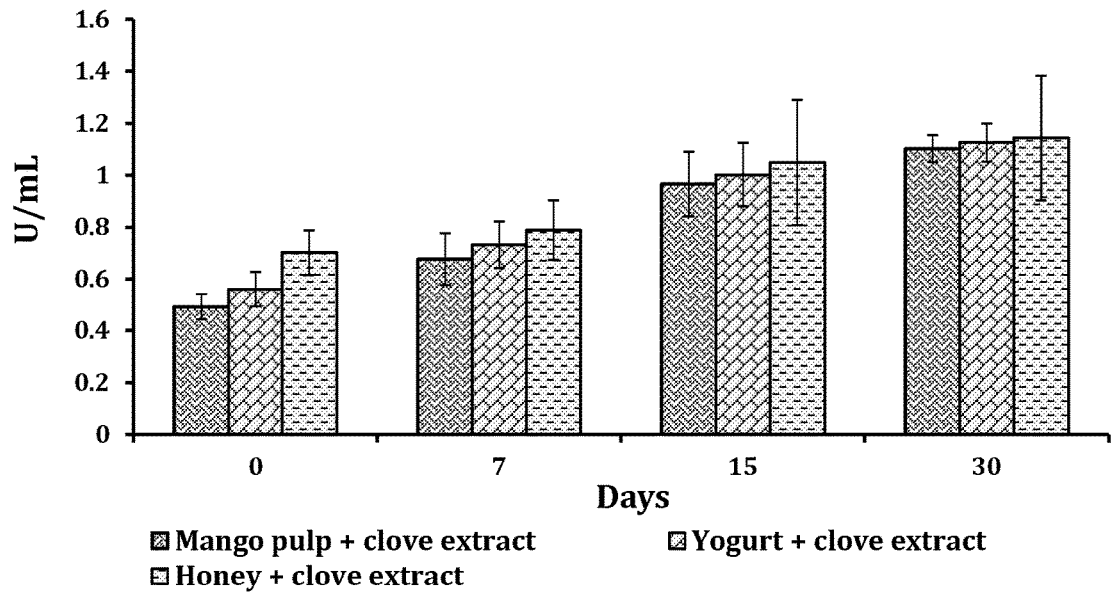
(Fig 8B)
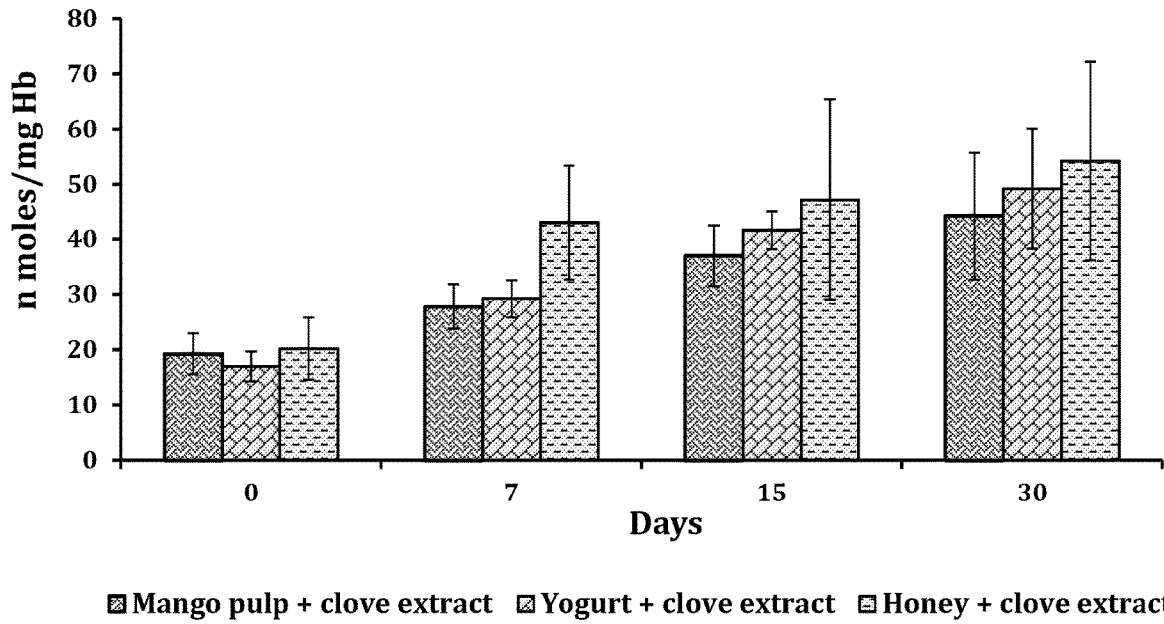

(Fig 8C)

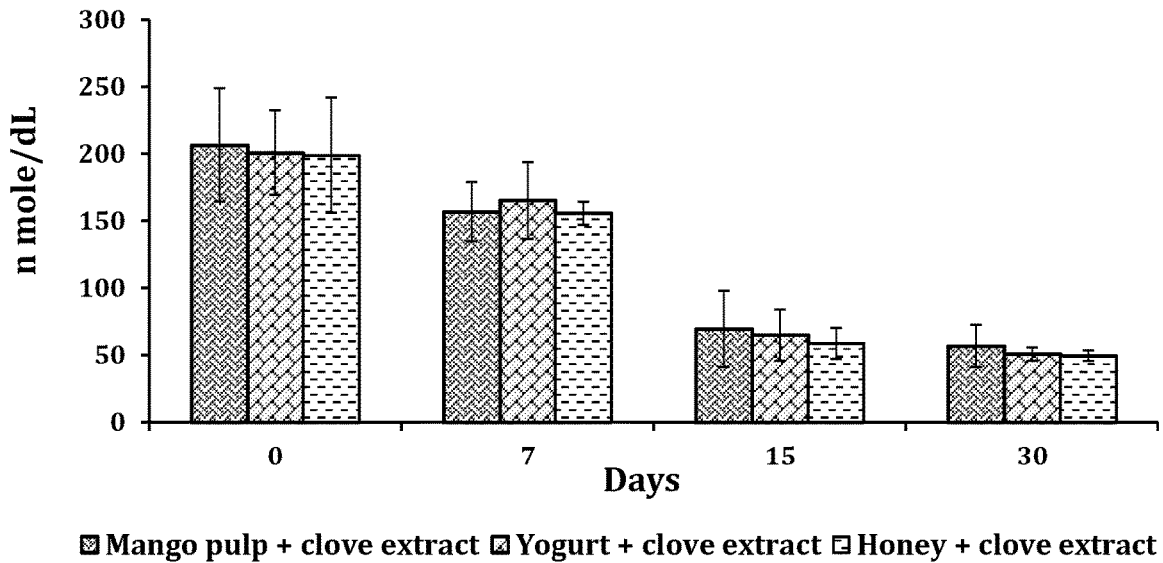

☒ Mango pulp + clove extract  ☒ Yogurt + clove extract  ☐ Honey + clove extract (A) Super oxide dismutase activity of clove extract impregnated on food beverages
(B) Reduced glutathione activity of clove extract impregnated on food beverages
(C) Lipid peroxidation activity of clove extract impregnated on food beverages FIG 9: (A&B): Effect of drinking plain water containing deflavoured Clove at 250 mg/150 mL/day for 15 days (Fig 9A)

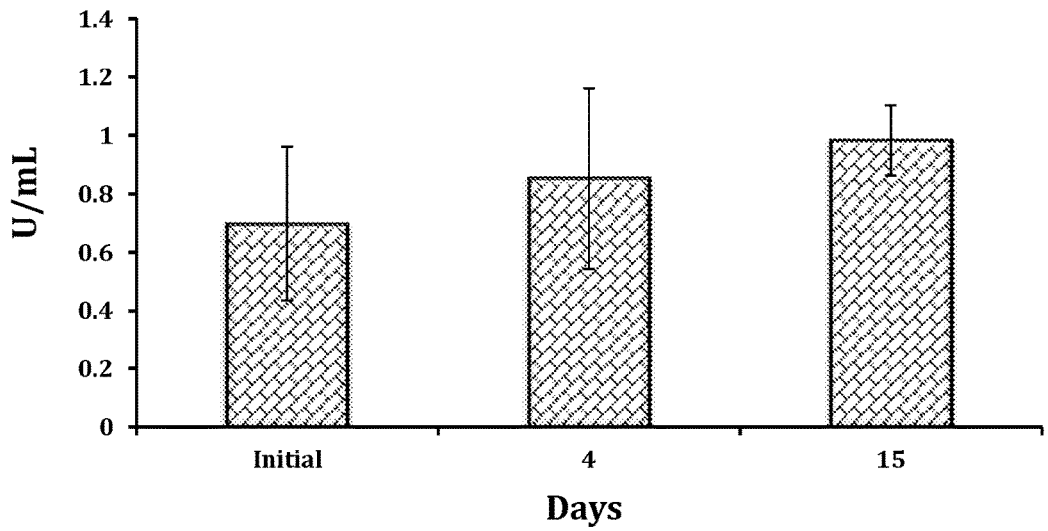

(Fig 9B)
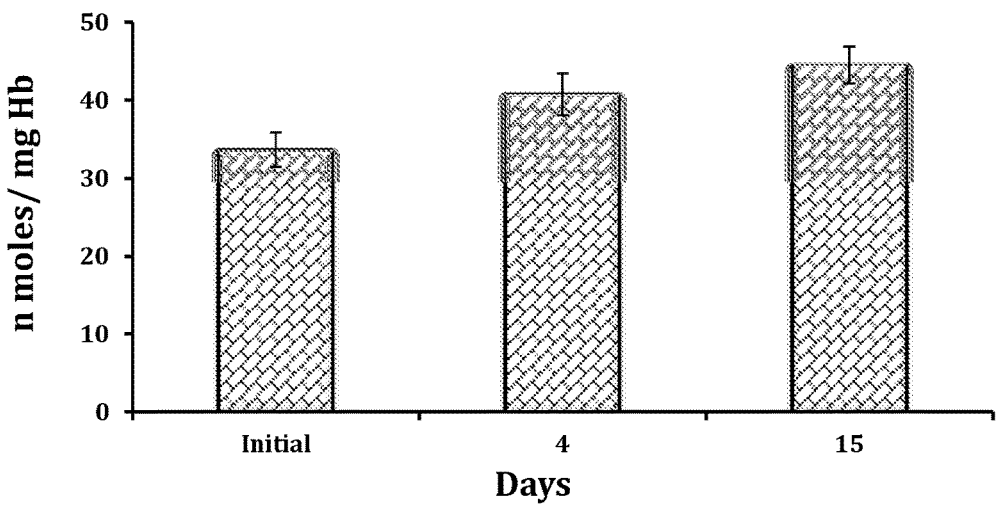
(A) Super oxide dismutase activity of clove extract in plain water; (B) Reduced glutathione activity of clove extract on plain water
FIG 10: (A, B & C): Effect of consumption of de-flavoured cinnamon extract impregnated breakfast cereal for 20 days
(Fig 10A)
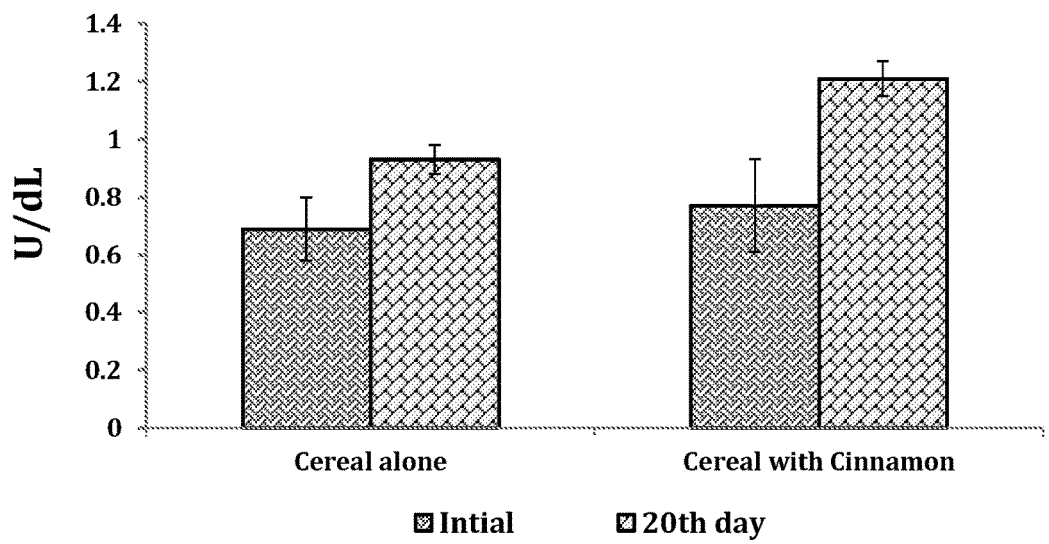

(Fig 10B)
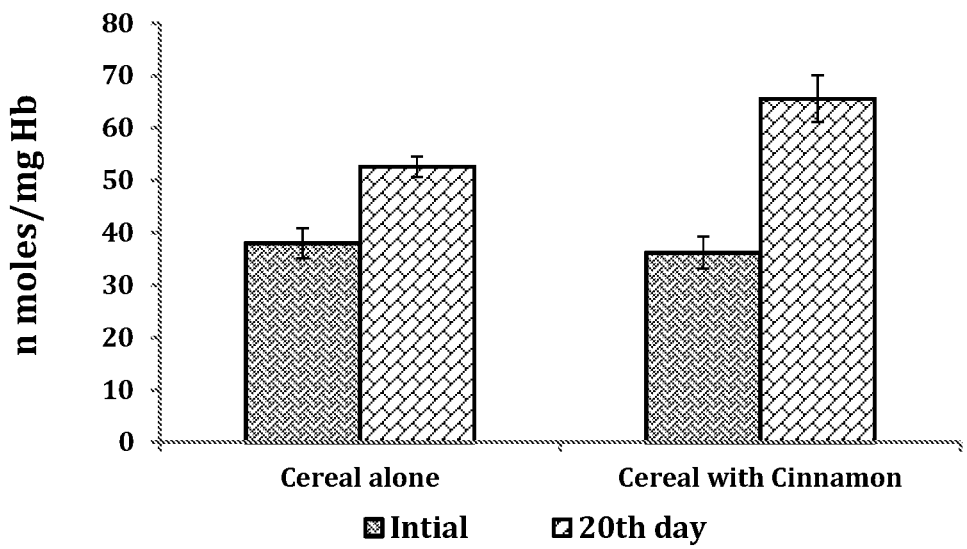
(Fig 10C)
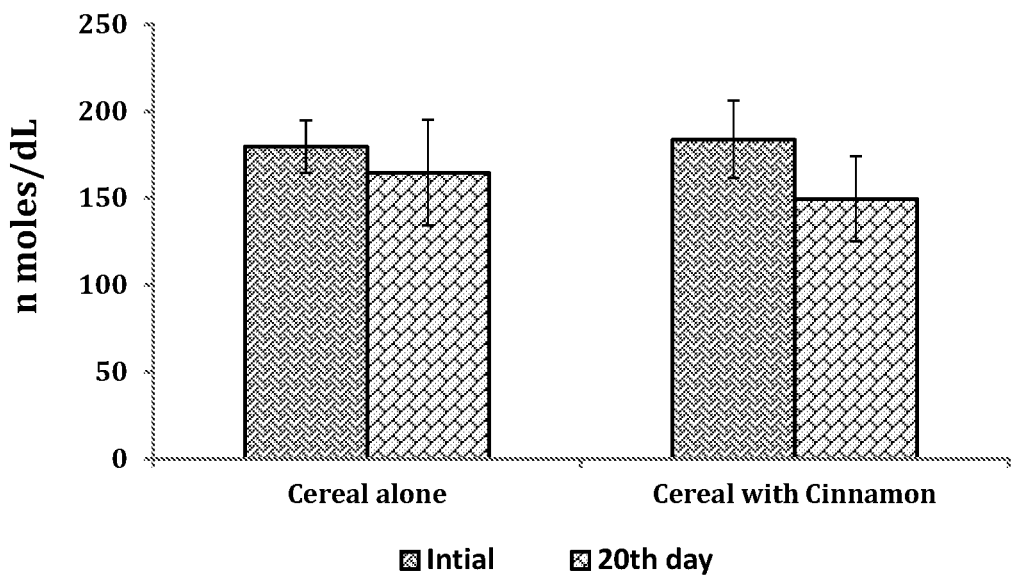
(A) Super oxide dismutase activity of cinnamon extract impregnated on Cereal
(B) Reduced glutathione activity of cinnamon extract impregnated on Cereal
(C) Lipid peroxidation activity of cinnamon extract impregnated on Cereal

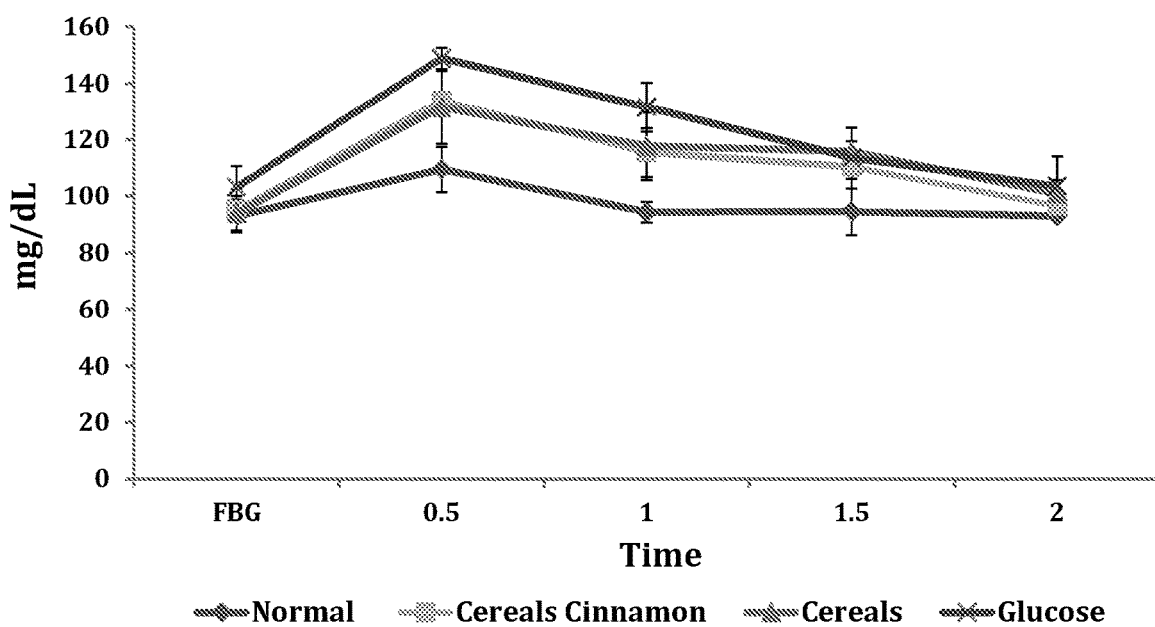
FIG 11: Effect of de-flavoured cinnamon extract impregnation upon the Glycemix Index level breakfast cereal

INSTANT WATER SOLUBLE BIOACTIVE DIETARY PHYTONUTRIENTS COMPOSITION OF SPICE/HERB EXTRACTS AND A PROCESS FOR ITS PREPARATION

FIELD OF THE INVENTION

The present invention relates to a method for the preparation of the instant water soluble, stable, phytonutrient rich spice/herb extracts exhibiting significant antioxidant and other bioactivities, in a ready to use form and a composition for beverage and food applications to deliver physiologically relevant amounts of phytonutrients per serving without taste or aroma issue and in organic quality. The composition derived in the present invention include the bioactive phytonutrient molecules along with its natural counter parts comprising mainly proteins, carbohydrates and dietary fibre of the spice and/or herb.

The present invention thus describes a method of phytonutrients extraction comprising solvent extraction, concentration, settlement, filtration and formulation of spice/herb derived phytonutrients suitable for the preparation of nutritional or functional food and/or beverages with enhanced nutritional quality, say antioxidant effect and bioactivity.

BACKGROUND OF THE INVENTION

Spices are rich in antioxidants and other bioactive phytochemicals, commonly referred to as phytonutrients. The bioactive compounds found in spices and herbs mainly include polyphenols, comprising flavonoids and their glycosides, polyphenolic acids and their derivatives, catechins and procyanidins, anthocyanins etc. Because spices have very low calorie content and are relatively inexpensive, they are reliable sources of antioxidants and other potential bioactive compounds in diet. There are many well studied reports that spices and herbs contain chockfull of antioxidant phytonutrients capable of providing better antioxidant protection and many other beneficial health guarding pharmacological activities in vivo. Many preclinical and clinical studies have shown that the phytochemicals in spices and herbs can provide a great deal of protection and even curing of many disease states such as metabolic syndromes and even chronic diseases like cancer, Alzheimer's etc. It has been proved that a plant-based diet can protect against chronic oxidative stress-related diseases and it has been shown that various chemical families present in dietary plants and their high antioxidant potential is primarily the reason for the beneficial effects.

A large number of research papers are available on various spices and herbs to demonstrate that they are rich in various types of phytochemicals possessing strong antioxidant and other pharmacological actions. Various extracts of such spices/herbs, namely water extract, alcohol extract, hydro-alcoholic extracts, acetone-water extracts and other polar and non-polar solvent extracts have been reported to possess beneficial effects. But most of these extracts were prepared in small scale of the order of 10 to 50 grams in solution or crude paste form and used for analysis immediately after their extraction.

No information regarding their formulation into various forms suitable for the commercial scale preparation, storage and uses are mentioned elsewhere. Further, these works are not considered the strong taste and aroma and volatile oil content in such extracts which very often limits their usage or consumption. Yet another issue that the research papers have not addressed is the solubility of spice/herb phytonutrients. Most of these antioxidant phytochemicals have very low solubility in water owing to their hydrophobicity and are not completely soluble in water. Aqueous insolubility, temperature instability under conditions of process like pasteurizations, instability of aqueous solutions during storage, and finally a convenient form of said extracts for storage with enough shelf life of not less than 12 months are the other major challenges in addition to aroma and pungency issues with regard to the preparation and functional use of spice/herb extracts.

Various in vitro, in vivo studies and clinical trials have shown that spice derived antioxidant phytonutrients from spices and herbs have beneficial pharmacological effects against many of the disease states; such as obesity, insulin resistance, anti-hypercholesterolemic, cancer, neurodegenerative diseases, gastrointestinal disorders etc. (Annu. Rev. Nutr. 2010. 30:14.1-14.27), (Current Cardiology Reviews, 2010, 6, 274-279) (Mol Neurobiol. 2011 October; 44(2): 142-159), (J Nutr Biochem. 2008 June; 19(6): 347-361).

Further, a number of publications/patents are also available about the extraction of antioxidants containing crude extracts and their antioxidant efficacy measurements using various in vitro and in vivo assays. These common extracts are prepared using water, alcohol, water-alcohol mixture and other organic solvents. (Food Chemistry, 118, 2010, 589-593, Nutrition Journal 2010, 9:3, WO/2013/057520, U.S. Pat. No. 5,985,352, US20100215783, WO/2013/049540, U.S. Pat. No. 5,525,260, WO/2007/130666.

Though these studies are useful to understand the various antioxidant molecules present in each spice extracts and the antioxidant efficacy of various extracts (such as water extract, alcohol extract etc.), no information are available to date regarding the formulation of such extracted antioxidants in a convenient stable and water soluble dosage form ready for the application in food/beverages/dairy products without the taste/pungency issue, and to trigger a beneficial physiological function. Even if extraction process have been studied, most of these studies have performed in vivo using capsules/tablets or even powders of antioxidant phytonutrient extracts or isolated phytochemicals of spices and herbs which are not suitable for food/beverage/diary applications. It is always better to incorporate such health guarding or promoting phytonutrients of spices/herbs in food/beverage matrices for general daily consumption to derive the health benefits. But, the consumption of spices and spice extracts containing standardized high levels of phytonutrients cause many issues due to their inherent taste (pungency, bitterness etc.), aroma, stability, water solubility, availability in food quality etc. No antioxidant phytonutrient-rich completely water soluble and stable extracts of spices/herbs capable of providing enough dosage (physiologically relevant amount of antioxidants or bioactive molecules/serving) in a cost-effective manner has reported so far. Further no one has addressed the issues of a stable and fully water soluble organic grade antioxidant rich spice/herb extracts suitable for the beverage/diary applications. No information about the solubility, formulation, antioxidant effect, stability, taste and aroma issues, sedimentation when used in beverages etc. have been disclosed.

The antioxidants disclosed in the research papers are not free from the strong aroma and pungent taste characteristic of the spices for easy impregnation in the beverage/diary matrix for consumption. Though some publications regarding the aqueous extracts, alcoholic extracts, hydro-alcoholic extracts and other solvent extracts of spices and their in vitro or in vivo antioxidant efficacies have reported in the literature, no information is available about their possible formulation water soluble, stable, convenient powder forms suitable for the ready incorporation into various powder or liquid based food/beverage/dairy products at physiologically relevant levels, without the aroma or taste issues.

SUMMARY OF THE INVENTION—INTRODUCTION

The present invention tackles the above problem and provides novel compositions of phytonutrient-rich extracts of spices/herbs as functional food/beverage ingredients and a process for its preparation. So, preparation of a formulation which is instantly soluble and shows no sedimentation on standing for weeks or months is a challenging task, which is addressed in this invention.

In the present invention, the above problems are tackled by adjusting the extraction solvent (water or ethanol or its mixtures), pre-treatment of the spice/herb (cutting, flaking, powdering etc.), extraction conditions (solvent ratio, temperature, and pressure and extraction time), and by formulation as a spray dried free flowing powder depending on the nature of the spice. De-oiling of spices (using steam distillation, Supercritical fluid extraction etc.) prior to aqueous or alcohol extraction can also be employed, depending on the spice.

The present invention came out from the understanding that the spices and herbs are rich in volatile antioxidant compounds (mainly oils containing terpenes and terpenoids) and non-volatile antioxidant compounds such as polyphenols (flavonoids and their glycosides, phenolic acids and their glycosides, terpenoid polyphenols, anthocyanins etc.). These polyphenols are mainly responsible for the antioxidant effects and are free from pungency. So, careful separation of volatile and non-volatile part of the spice constituents and their optimized blends are developed in the present study to derive fully water soluble antioxidant-rich and bioactive extracts of spices. An optimized extraction process, concentration of the miscella (the solvent containing the extractives of spices) under controlled conditions to designated total dissolved solids (TDS) levels, settling, filtration, blending with excipients such as maltodextrin and sugar/salt syrup followed by spray drying was employed to make antioxidant encapsulated extract powders of particle size 125±25 μm particles capable of dissolving in the water to produce particles of around 1.0±0.4 μm size for complete dissolution.

SUMMARY OF THE INVENTION PART 1—OBJECTS OF THE INVENTION

An object of the present invention is to develop a suitable method for the extraction of specific compositions of spice and/or herb extractives containing the bioactive molecules along with their natural matrices containing proteins, carbohydrates and dietary fibre in a water soluble form and the purification of these phytonutrients in spices/herbs using only water and ethanol, either alone or in combination to produce bioactive green extracts of organic quality.

Another object of the present invention is to develop a method for the production of phytonutrient rich spice and herb extract without the problem of strong aroma or flavour characteristic of the spices and herbs is provided.

Yet another object of the instant invention is to develop a method of phytonutrient extraction process for spices/herbs-rich in volatile oil such as clove, nutmeg, mace etc. Supercritical fluid extraction or steam distillation or sometimes solvent extraction using lower aliphatic alkanes (hexane, heptane. cyclohexane etc.) or a combination of alkane and aliphatic ketone (e.g.: hexane/acetone) are used for this purpose. This helps to remove the pungent and strong smelling oils and oleoresin part without affecting the non-volatile antioxidants. Extraction time, temperature, pressure and solvent need to be adjusted to protect the non-volatile antioxidants.

Another object of the present invention is to develop a method of extraction of phytonutrients for spices like cinnamon and clove containing stable phytonutrients like polyphenols, procyanidins and hydrolysable tannins wherein they are subjected to selective organic solvent extraction to remove the aroma and flavour components and the resulting residues are subjected to further extraction process to produce water soluble antioxidant phytonutrient extracts in water soluble form. Such spices can also be subjected to direct water extraction followed by formulation into water soluble extracts.

Yet another object of the present invention is to develop a process to produce spice/herb extracts rich in phytonutrients capable of impregnating in food item such as honey to provide a nutritional bread spread or similar applications, (e.g.: cinnamon in honey). Such blends are not possible with cinnamon powder or conventional extracts due to miscibility issues.

Another objective of the present invention is to develop a process to produce an instantly water soluble phytonutrient-rich highly antioxidant extract powder of spices/herbs which do not cause any sedimentation during storage for 1 week to 6 months in water solution at physiologically relevant dosage of 100 to 500 mg per 180 mL.

Another object of the present invention is to develop a process to produce instant water soluble free flowing stable powder of various spices with tailored aroma and taste profile for various food/beverage applications at 100 to 500 mg/serving level sufficient to trigger a healthy or positive health benefit on human beings.

Another object of the present invention is to develop a water soluble spice and/or herb extract rich in antioxidant phytochemicals was provided for functional food, medical food and cosmecutical applications.

Another object of the present invention deals with the development of a formulation for spice/herb antioxidants in ready to use powder or liquid form without any problem of settlement, precipitation, colour change, odour change, microbial contamination etc. during storage. A methodology is developed whereby the phytonutrients of spices and herbs can be conveniently delivered for betterment of health, as a beverage or diary food product or as dietary supplement without the problem of taste/aroma issue which normally prevents the consumption of spices and herbs, unlike the fruit and vegetables. Further an organic quality spice/herb phytonutrient extracts for beverage/diary applications is developed. The spice/herb phytonutrients are provided at convenient dosage suitable for triggering beneficial physiological response such as antioxidant status of blood serum, reduction of oxidative stress, reduction of inflammatory markers, enhancement in digestion, ulcer curative property, gastrointestinal health, blood sugar management potential, or hypolipidemic effects, or diuretic as seen from the animal study data, in vitro assays or human studies. A beverage/diary ingredient of spices/herbs is produced which is capable of providing 1000 to 5000 ORAC (Oxygen Radicle Absorbance Capacity) value when consume a serving of food/beverage containing 250 to 500 mg spice extract. Further a fully water soluble spice/herb phytonutrients is provided which is capable of fortifying the nutritional value of other food/beverage products such as fruit juices, milk shakes, etc. without taste/aroma issue. A stable form of spice/herb phytonutrients such as antioxidants to produce antioxidant rich bottled drinking water has been developed. For example, cumin-water or ginger water capable of providing 1000 to 3000 ORAC per a 1 lit bottle of water. The examples given here do not limit the scope of applicability, since a large number of food/beverage/diary applications can be envisaged with the novel extracts detailed in the present investigation to trigger a health pharmacological response upon its consumption on a regular basis, depending upon the effect of interest.

SUMMARY OF THE INVENTION PART 2

The present invention relates to a method for the preparation of the instant water soluble, stable, phytonutrient rich bioactive spice/herb extracts in ready to use form and a composition for beverage/food applications to deliver physiologically relevant amounts of phytonutrients per serving without taste or aroma issue and in organic quality. Thus briefly the present invention describes solvent extraction, concentration, filtration and formulation of spice/herb derived phytonutrient antioxidants suitable for the preparation of nutritional or functional food/beverages.

The important aspects of the present invention are to provide,

A suitable method for the extraction of specific compositions of spice and/or herb extractives containing the bioactive molecules along with their natural matrices containing proteins, carbohydrates and dietary fibre in a water soluble form and the purification of these phytonutrients in spices/herbs using only water and ethanol, either alone or in combination to produce bioactive green extracts of organic quality.

A ready to use formulation of the isolated phytonutrient-rich extracts into instant water soluble forms (powder and liquid) with customised taste and aroma, without imparting strong taste or aroma characteristic of the spice and/or herb and without any settlement during storage of 1 to 3 months.

In one of the aspect of the present invention, a method for the production of a water soluble phytonutrient rich spice and herb extract without the problem of strong aroma or flavour characteristic of the spices and herbs is provided.

In another aspect of the present invention, the spice such as coriander, cumin, fennel, cinnamon, nutmeg, mace, celery, cardamom, etc. are mechanically reduced to smaller particles by way of cutting, flaking and powdering. The particles thus formed measure about 1±0.5 mm in size.

In another aspect the spice and/or herb particles thus obtained are subject to hydro-ethanol or aqueous extraction. For this about 3 to 5 times volume of solvent, (e.g.: water-ethanol mixture containing various percentage of solvents, preferably, 30:70 v/v) is added to the spice/herb particles. The solvent along with the spice/herb particles are circulated with an agitator in a stainless steel vessel. After 2 hours of circulation, the solvent is allowed to settle for another 1 hr and filtered. The clear filtrate thus obtained is stored in a vessel. The extraction is repeated 3 to 5 times and the filtrate is stored collectively.

In another aspect of the present invention the powdered spice and or herb is subjected to ultra-sonication applied as pulses of 1 to 5 min duration without raising the temperature above 50° C.

In another aspect of the present invention the powdered spice and or herb is subjected to under microwave assisted solvent extraction at conditions of temperature below 50° C.

In another embodiment of the invention if the spice is rich in volatile oil such as clove, nutmeg, mace etc., prior to the extraction step they are subjected to supercritical fluid extraction or steam distillation or sometimes solvent extraction using lower alkanes or cylcoalkanes (hexane, heptane. cyclohexane etc.) or a combination of alkane and aliphatic ketone (hexane/acetone) can be used. This helps to remove the pungent and strong smelling oils and oleoresin part without affecting the non-volatile antioxidants. Extraction time, temperature, pressure and solvent need to be adjusted to protect the non-volatile antioxidants.

In another embodiment of the invention spices like cinnamon and clove containing stable phytonutrients like polyphenols and procyanidins are subjected to selective organic solvent extraction to remove the aroma and flavour components and the resulting residues are further extracted to produce water soluble antioxidant phytonutrient extracts in water soluble form.

In another aspect, the lower alcohols like methanol, ethanol are used in combination with water at various proportions of ethanol/water ranging from 20:80 to 80:20 v/v. Acetone/water mixture at various proportions, most preferably 70:30 v/v is also used to extract antioxidants.

In yet another aspect of the present invention, pure water at elevated temperature of about 60 to 90° C. may also be used as a solvent for the extraction of bioactive phytonutrients containing extracts.

In another aspect, the ethanol in the filtrate is evaporated slowly at temperature 35 to 50° C. using a 'forced circulation evaporation' at 10 to 20 Lit/hr or spinning cone column evaporation at 100 Lit/hr is critical to avoid precipitation and to avoid the thermal degradation of the antioxidants. The ethanol is evaporated and further concentrated the aqueous solution to a Total Dissolved Solids (TDS) of not more than 20 to 35% and allowed cool and settle at 15° C. for 4 to 8 hr. to affect the precipitation of low solubility phyto constituents from the spice matrix.

In another embodiment of the present invention the extract after evaporation is cooled at a temperature of 15° C. for 3 to 6 h, more preferably 4 h is very critical to avoid the suspended matter, colloidal particles, precipitates, and other particles of low solubility in water.

In another aspect of the invention the phytonutrient rich extract are further concentrated and separated by further subjecting to chromatographic separation using an adsorption or ion-exchange chromatography types with a resin comprising divinyl benzene-cross linked polystyrene or polyamide as the stationary phase and lower alcohols and acetone either alone or in combination as eluents.

In yet another aspect of the present invention the concentrated extract rich in phytonutrients in aqueous solution is again filtered through about 275 to about 350 micron filter to avoid any sedimentation or precipitate.

In another aspect, the total dissolved solids (TDS) of the clear solution obtained after filtration is checked and blended with 5 to 30% w/w of additives such as water soluble maltodextrin, 1 to 3% w/w of carbohydrates like glucose syrup or cone syrup or sorbitol and 0.5% w/w of sugar ester and homogenized using a high pressure homogenizer at 250 to 400 bar pressure.

In another aspect of the invention the cooled extract is blended with additives having encapsulating properties and water solubility enhancing properties is very important to protect the spice/herb phytonutrients and antioxidants for more storage, heat or light stability. The sugar ester helps to enhance the solubility of the spice antioxidants in some cases.

In yet another aspect of the invention the extract and the additives are homogenized at 250 to 1000 bars, preferably at 250 to 450 bars to effect the good encapsulation. This is further filtered through a filter of about 275 to about 350 micron pore size.

In another aspect of the invention, the additives added for spray drying can be different, depending on the nature of the spices which includes, but not limited to maltodextrin, water soluble starches, water soluble modified starches, gum acacia, xanthum gum, cyclodextrins, simple carbohydrates like glucose, fructose, lactose, sucrose etc and their syrups, sorbitol, etc. Blends without these carbohydrates, especially using organic acids of beverage quality citric acid, oxalic acid etc. or salt or any such ingredient which may possibly use in food/beverages can also be used.

In another aspect, solvent filtrate blended with the additives is further spray dried or freeze dried to free flowing fully water soluble spice/herb antioxidant powder containing high levels of antioxidants like polyphenols, flavonoids and their glycosides, catechins and procyanidins, phenolic acids and their derivatives and anthocyanins.

In another aspect of the invention the homogenized blend is spray dried at 5 to 20% brix, preferably at low brix of around 6 to 8% is desired to make water soluble antioxidant powders. The spray drying is preferably carrying out at Total Dissolved Solid (TDS) levels of 5 to 20% v/v, depending on the spice extract. For example, cinnamon extract is spraying at 5 to 6%, whereas the coriander can be done at 20% TDS.

In another embodiment of the invention, other powder manufacturing methods such as freeze drying, microwave evaporations, etc. can also be used. Low TDS of around 6 to 8% helps to produce less particle size powder which is amorphous and freely soluble.

In another aspect of the invention oil and flavour components rich spices like Clove buds, Cardamom and ginger can be extracted in different steps to produce volatile and non-volatile components and can be further blended to provide instant water soluble phytonutrient extracts with tailored flavour profile suitable for various food/beverage applications.

In another aspect of the present invention a spice/herb extracts rich in phytonutrients capable of impregnating in food item such as honey to provide a nutritional bread spread or similar applications is developed. For example, cinnamon in honey. Such blends are not possible with cinnamon powder or conventional extracts due to miscibility issues.

In another aspect of the present invention, an instantly water soluble phytonutrient-rich highly antioxidant extract powder of spices/herbs is produced which do not cause any sedimentation during storage for 1 week to 6 months in water solution at physiologically relevant dosage of 100 to 500 mg per 180 mL.

In another aspect, instant water soluble free flowing stable powder of various spices with tailored aroma and taste profile was provided for various food/beverage applications at 100 to 500 mg/serving level sufficient to trigger a healthy or positive health benefit on human beings.

In another aspect of the present invention, a water soluble spice and/or herb extract rich in antioxidant phytochemicals was provided for functional food, medical food and cosmecutical applications.

In another aspect of the present invention a method for producing completely water soluble spice/herb phytonutrient extracts capable of triggering a beneficial pharmacological effect such as antioxidant, anti-inflammatory, blood-sugar management, lipid profile management and or digestive properties is developed depending on the spice/herb used.

In another aspect of the present invention a unique process for producing biologically active water soluble spice extracts suitable for consumption or impregnation in food and beverages without having the problem of taste, aroma, stability or aqueous solubility is developed.

In another aspect of the present invention a stable composition of spice/herbs phytonutrients having a minimum of about 12 month's shelf life for functional food/beverage or medicinal food/beverage applications and also for nutraceutical/cosmecutical applications have been developed.

According to yet another aspect, the present invention deals with the development of a formulation for spice/herb antioxidants in ready to use powder or liquid form without any problem of settlement, precipitation, colour change, odour change, microbial issues etc. during storage. A methodology is developed whereby the phytonutrients of spices and herbs can be conveniently delivered for betterment of health, as a beverage or diary food product or as dietary supplement without the problem of taste/aroma issue which normally prevents the consumption of spices and herbs, unlike the fruit and vegetables. Further an organic quality spice/herb phytonutrient extracts for beverage/diary applications is developed. The spice/herb phytonutrients are provided at convenient dosage suitable for triggering beneficial physiological response such as antioxidant status of blood serum, reduction of oxidative stress, reduction of inflammatory markers, enhancement in digestion, ulcer curative property, gastrointestinal health, blood sugar management potential, or hypolipidemic effects, or diuretic as seen from the animal study data, in vitro assays or human studies. A beverage/diary ingredient of spices/herbs is produced which is capable of providing 1000 to 5000 ORAC (Oxygen Radical Absorbance Capacity) value when consume a serving of food/beverage containing 250 to 500 mg spice extract. Further a fully water soluble spice/herb phytonutrients is provided which is capable of fortifying the nutritional value of other food/beverage products such as fruit juices, milk shakes, etc. without taste/aroma issue. A stable form of spice/herb phytonutrients such as antioxidants to produce antioxidant rich bottled drinking water has been developed. For example, cumin-water or ginger water capable of providing 1000 to 3000 ORAC per a 1 lit bottle of water.

In another aspect of the present invention a process and formulation of spice and/or herb phytonutrient extracts is prepared in organic quality with customised flavour and/or taste profile for various food/beverage applications.

In yet another aspect, the present invention takes the spices and herbs to beyond flavours. The medicinal and nutritional values of spices/herbs are made available for food applications without flavour issues or with tailored flavour effects. For example, cinnamon flavoured yogurts rich in cinnamon polyphenols.

BRIEF DESCRIPTION OF DRAWINGS

FIG. 1: Polyphenol content of various de-flavoured spice extracts.

FIG. 2: In vitro antioxidant effects of water-soluble spice phytonutrient extracts FIG. 3: Free radical scavenging activity of water-soluble spice phytonutrient Extracts FIG. 4: Effect of de-flavoured cumin extract incorporated potato chips on the antioxidant activity.

FIG. 5: Evaluation of In vivo anti-inflammatory potential of water soluble, de-flavored Clove extract FIG. 6: Antidiabetic activity of spice extracts (Cinnamon, Clove & Cumin) by glucose tolerance test FIG. 7: Hypolipidemic activity of clove extract in fat diet induced obese models FIG. 8: (A, B & C): Effect of consuming water soluble de-flavoured clove extract impregnated food on oxidative stress of healthy human volunteers.

FIG. 9: (A & B): Effect of drinking plain water containing de-flavoured Clove at 250 mg/150 mL/day for 15 days FIG. 10: (A, B, & C): Effect of consumption of de-flavoured cinnamon extract impregnated breakfast cereal for 20 days FIG. 11: Effect of de-flavoured cinnamon extracts impregnation breakfast cereal on the Glycemix Index level.

DETAILED DESCRIPTION OF THE INVENTION

For the purposes of the following detailed description, it is to be understood that the invention may assume various alternative variations and step sequences, except where expressly specified to the contrary. Moreover, other than in any operating examples, or where otherwise indicated, all numbers expressing, for example, quantities of ingredients used in the specification are to be understood as being modified in all instances by the term "about". It is noted that, unless otherwise stated, all percentages given in this specification and appended claims refer to percentages by weight of the total composition.

Thus, before describing the present invention in detail, it is to be understood that this invention is not limited to particularly exemplified systems or process parameters that may of course, vary. It is also to be understood that the terminology used herein is for the purpose of describing particular embodiments of the invention only, and is not intended to limit the scope of the invention in any manner.

The use of examples anywhere in this specification including examples of any terms discussed herein is illustrative only, and in no way limits the scope and meaning of the invention or of any exemplified term. Likewise, the invention is not limited to various embodiments given in this specification.

Unless otherwise defined, all technical and scientific terms used herein have the same meaning as commonly understood by one of ordinary skill in the art to which this invention pertains. In the case of conflict, the present document, including definitions will control.

It must be noted that, as used in this specification and the appended claims, the singular forms "a," "an" and "the" include plural referents unless the content clearly dictates otherwise. Thus, for example, reference to a "solvent" may include two or more such solvents.

The terms "preferred" and "preferably" refer to embodiments of the invention that may afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the invention.

As used herein, the terms "comprising" "including," "having," "containing," "involving," and the like are to be understood to be open-ended, i.e., to mean including but not limited to.

Unless defined otherwise, all technical and scientific terms used herein have the same meaning as commonly understood by one of ordinary skill in the art to which the invention pertains.

The term "miscella" as used herein refers to a solvent containing the extractives of spices.

All of the current methods in the art suffer from the problem of the difficulty of getting rid of the unfavourable taste and aroma issues of spices (pungency, smell, etc.), mainly owing to the volatile oils. The present invention describes a novel methodology to extract, formulate, standardise and use spice phytonutrients as functional ingredients, without the organoleptic issues or sensory limitations.

Thus, the objective of the present invention is to provide fully and instantly cold and hot water soluble bioactive phytonutrient rich extracts from spices and herbs without the problem of pungency (taste) or smell to consume physiologically relevant dosages per serving when used as beverage or food or diary item or as a capsule or tablet or syrup etc., which does not undergo sedimentation stable.

Advantageously in the present invention a novel and inventive extraction process have been developed to extract phytonutrients from spices and/or herbs which produce water soluble phytonutrient extracts which can be readily blended with the food, water and beverages as well as in medicines and cosmetic products.

Another advantage of the present invention is the production of phytonutrient extract without aroma or any pungent smell. This biologically active water soluble spice extracts suitable for consumption or impregnation in food and beverages are without having the problem of taste, aroma, and are stable and aqueous soluble. Thus the completely water soluble spice/herb phytonutrient extracts in the absence of any emulsifiers and are capable of triggering a beneficial pharmacological effect such as antioxidant, anti-inflammatory, blood-sugar management, lipid profile management and or digestive properties, depending on the spice/herb used.

In one aspect of the present invention a process for the preparation of de-flavoured and de-aromatised food and beverage additives rich in health beneficial bioactive phytonutrients from spices and/or herbs suitable for the impregnation at sufficiently high concentrations per serving to trigger a health beneficial pharmacological effect has been developed wherein the said process comprises the steps of
 a) mechanically reducing the particle size of the spice and/or herb
 b) subjecting the product obtained from step (a) to a solvent extraction process
 c) filtering the extract to separate the solvent extract and residue
 d) concentration of the solvent extract from step (c) to obtain phytonutrient rich extract
 e) cooling, settling and filtering the extract obtained from step (d)
 f) Blending, homogenizing and filtering the concentrated extract obtained from step (e) with additive and/or natural excipients.
 g) Spray drying the blended and filtered composition obtained from step (f)

In an embodiment of the invention the herb and/or spice to be extracted is subjected to a pre-treatment wherein it is cut/flaked/powdered to appropriate particle size, to allow the penetration of the solvents into the spice matrix to leach the phytonutrients. Thus the spices and/or herbs are cut and/or flaked or powdered to 2±0.5 µm particle sizes.

The present procedure can be used for other spices and herbs including, but not limited to Coriander, Clove, Fennel, ginger, Caraway, nutmeg, mace, Cardamom, cumin, cinnamon, Amla (*Emblica*), Moringa (*Moringa olifera*), Tribulus, Fenugreek, Cocoa, Coffee, turmeric, etc.

In another embodiment of the instant invention, if the spice is rich in volatile oil such as clove, nutmeg, mace etc., supercritical fluid extraction or steam distillation or sometimes solvent extraction using lower alkanes or cycloalkanes (hexane, heptane. cyclohexane) or a combination of alkane and aliphatic ketone (hexane/acetone) are used. This helps to remove the pungent and strong smelling oils and oleoresin part without affecting the non-volatile antioxidants. The extraction time, temperature, pressure and solvent used have to be adjusted to protect the non-volatile antioxidants. The de-oiled spice thus produced can further be subjected to supercritical extraction at higher pressures or solvent extraction to produce flavour rich components called oleoresin. The spent obtained after the oleoresin separation can further be extracted with ethanol water or acetone water or using water alone, as explained in examples 1, 2 and 3 to provide non-volatile phytonutrients-rich extracts (such as polyphenol rich extracts) and can be further formulated with definite quantity of the essential oil and flavour components to produce water soluble spice extracts with instant water solubility.

In yet another embodiment of the invention in the case of certain spices like cinnamon and clove containing stable phytonutrients like polyphenols and procyanidins are subjected to selective organic solvent extraction to remove the aroma and flavour components and the resulting residues are further subjected to extraction to produce water soluble antioxidant phytonutrient extracts in water soluble form.

In another aspect of the present invention after mechanically reducing the size of the spice and/or herb, they are subjected to solvent extraction. The solvent used in this step are selected from the group consisting of an organic solvent such as lower aliphatic alcohols, (e.g.: methanol, ethanol), lower aliphatic ketones (e.g.: acetone, propanone), or water and/or their mixtures either alone or in combination. The water content of the alcohol/water mixture or acetone/water mixture used in the extraction varies from 20 to 80%, or even 100%, most preferably 30 to 40%. Most of the spice and/or herb antioxidants have best solubility in these solvent systems which help the quantitative extraction. When the extraction is carried out with acetone/water mixture, the ratio ranges from 60:40 to 80:20 v/v. The ratio of water and solvent in the aqueous solution ranges from about 10:90 to 90:10 v/v. The extraction also used pure water at an elevated temperature of about 60 to about 90° C. The ratio of the spice and/or herb to the aqueous solvent mixture ranges from about 1:3 to about 1:5 w/v. During the extraction the flaked and/or powdered spice and/or herb is agitated for about 2 to about 3 hours. The extraction can also be done by subjecting the powdered spice and or herb to ultra-sonication applied as pulses of 1 to 5 min duration without raising the temperature above 50° C. The extraction can also be done by subjecting the powdered spice and or herb microwave conditions at temperature preferably below 50° C.

In another aspect of the invention the extract containing the phytonutrients obtained by the extraction process are filtered to separate the extract from the residues.

In another aspect of the present invention evaporation of alcohol or organic solvent like acetone at a temperature range of 35 to 60° C., preferably at 45 to 50° C., most preferably at 40 to 45° C. is carried out which results in the concentrated extract with less than 100 ppm ethanol level, or less than 25 ppm in case of acetone, without precipitation of the antioxidant components. The solvent residues may otherwise trap in the final extract powder which will make it not suitable for food/pharmacological applications.

In detail, the extract is subjected to slow evaporation of the solvent using a 'forced circulation evaporation' at 10 to 20 L/hr or spinning cone column evaporation at 100 L/hr is critical to avoid precipitation. Further evaporating the solvent from extract is carried out at a pressure of about 600 mmHg to about 750 mmHg. The water solution thus obtained after alcohol or acetone evaporation need to be further concentrated to 15 to 35% total dissolved solid (TDS) level, more importantly to 20 to 25% to affect the precipitation of low solubility phyto constituents from the spice matrix. The concentrated extract has ethanol in the range of about 2000 to about 100 ppm and acetone in a range of about 25 to 50 ppm acetone. The extract after solvent evaporation has a total dissolved solid (TDS) content of about 15% to about 35% more preferably to about 20% to about 25%.

In one embodiment of the invention the concentrated extract rich in phytonutrients are filtered and directly blended with the additives.

In another embodiment of the invention the extract after evaporation is subjected to chromatographic separation of its components. For this, an absorption chromatography or ion exchange chromatography with a stationary phase comprising a resin consisting of divinyl benzene-cross linked polystyrene or polyamide is used. Lower alcohols and acetone either alone or in combination with water are usually used as eluents. After eluting the different components of the extract, they are concentrated by evaporating the solvents as described above and are filtered and blended with additives and/or excipients.

In another aspect the concentrated extract is further cooled at a temperature of 15±2° C. for 3 to 6 hr, more preferably 4 hr is very critical to avoid the suspended matter, colloidal particles, precipitates, and other particles of low solubility in water.

In yet another aspect of the present invention the cooled extract is filtered using about 275 to about 300±25 micron cloth filter or the like which is essential to remove the precipitates or insoluble. The concentrated extract has a total dissolved solid (TDS) content of about 4 to about 20% w.

The phytonutrients in the final standardised water soluble extract contains polyphenols such as flavanols, flavonoids, flavanones, procyandins, stilbenes etc., volatile oils, terepenoids, alkaloids, fatty acids, fatty alcohols, saponins, anthocyanins, carotenoids, chlorophylls etc. It has volatile oil content of about 0.1 to 1.0%.

Advantageously, in an embodiment of the present invention the filtered, cooled and concentrated extract is blended with additives having encapsulating properties and water solubility enhancing properties to protect the spice/herb phytonutrients and antioxidants for more storage, heat or light stability. Thus the blending of extract is carried out with suitable natural excipients selected from starch, cellulose, sugar, citric acid.

In another aspect of the invention the total dissolved solids (TDS) of the clear solution obtained after filtration is checked and blended with 5 to 30% w/w of additives such as water soluble maltodextrin, 1 to 3% w/w of carbohydrates like glucose syrup or conc syrup or sorbitol and 0.2 to 1% w/w of sugar ester and homogenized using a high pressure homogenizer at 250 to 400 bar pressure. The blended product is once again filtered through a filter having a pore size of about 275 to about 350 microns.

In another embodiment of the invention the extracts are dried by subjecting to other powder manufacturing methods such as freeze drying, microwave evaporations, etc. Low TDS of around 6 to 8% helps to produce less particle size powder which is amorphous and freely soluble.

The present concentrated and filtered extract is a stable composition of spice/herbs phytonutrients having a minimum of about 12 month's shelf life for functional food/beverage or medicinal food/beverage applications and also for nutraceutical/cosmecutical applications.

In embodiment of the present invention the extract with the additives are homogenized at 250 to 1000 bar, more preferably at 250 to 400 bar to effect the good encapsulation. The homogenized mixture is finally spray dried at 5 to 20% brix, preferably at low brix of around 6 to 8% to make water soluble antioxidant powders.

In another aspect of the invention the homogenized blend is spray dried at 5 to 20% brix, preferably at low brix of around 6 to 8% is desired to make water soluble antioxidant powders. The spray drying is preferably carrying out at Total Dissolved Solid (TDS) levels of 5 to 20% v/v, depending on the spice extract. For example, cinnamon extract is spraying at 5 to 6%, whereas the coriander can be done at 20% TDS.

In another aspect of the invention, the additives added for spray drying can be different, depending on the nature of the spices which includes, but not limited to maltodextrin, water soluble starches, water soluble modified starches, gum acacia, xanthum gum, cyclodextrins, simple carbohydrates like glucose, fructose, lactose, sucrose etc. and their syrups, sorbitol, etc. Blends without these carbohydrates, especially using organic acids of beverage quality citric acid, oxalic acid etc. or salt or any such ingredient which may possibly use in food/beverages can also be used.

The extract of the present invention is a unique composition of spice/herbs phytonutrients capable of impregnating in food, beverages, plain drinking water, medicines and cosmetics. Such as dairy products, energy drinks, beverage sachets, ready to use powder drinks, juices, cookies, breakfast cereals, smoothie, snacks etc. for making them healthy and to trigger a healthy pharmacological effect upon its continuous consumption.

In an embodiment, the present invention provides various unique blends and applications to make a range of nutritional and antioxidant rich beverages or food products such as normal drinking bottled water, juices, carbonated beverages, sachets, milk shakes, ice creams, yogurts, soups, honey, etc.

The extraction, evaporation, blending and final spray drying is very important as these steps are used to tailor-make the aroma and/or taste of the extract powders. The final extract powders are generally standardized to 1±0.4% Volatile oil content level to produce the unique mouth feel of the spice. It varies from 0.1 to 5%, depending on the final usage.

The resulting final product show a polyphenol content of 1 to 50% as Gallic acid equivalents (depending on the spice, extraction solvent and final formulation), when measured using standardized Folin-Ciocaltue method. The extract powders are exhibiting antioxidant and free radical scavenging properties when measured by various antioxidant assays such as ORAC (oxygen radical absorbing capacity assay), CAP-e (cellular antioxidant protection at erythrocyte models), DPPH (2,2,-diphenyl-1-picryl hydrazyl assay), ABTS (2',2-azino-bis-3-ethyl benzthiazoline 6-sulphonic acid assay), FRAP (Ferric reducing ability of plasma assay), MDA (Lipid peroxidation) etc. assays. The water soluble antioxidant rich spice extracts thus produced shows blood sugar management potential as seen from the Glucose tolerance test, lowers both FBG (fasting blood sugar) and PPG (post prandial blood glucose), 2 hr after meals. The extracts were shown to have digestive properties and provide comfort in situations of gastritis and overheating. These extracts also have anti-inflammatory actions. Thus provide functional food ingredient benefits.

In another embodiment of the present invention a spice/herb extracts rich in phytonutrients capable of impregnating in food item such as honey to provide a nutritional bread spread or similar applications is developed. For example, cinnamon in honey. Such blends are not possible with cinnamon powder or conventional extracts due to miscibility issues.

In another embodiment, an instantly water soluble phytonutrient-rich highly anti-oxidative extract powder of spices/herbs is produced which do not cause any sedimentation during storage for 1 week to 6 months in water solution at physiologically relevant dosage of 100 to 500 mg per 180 mL.

In another embodiment, instant water soluble free flowing stable powder of various spices with tailored aroma and taste profile was provided for various food/beverage applications at 100 to 500 mg/serving level sufficient to trigger a healthy or positive health benefit on human beings.

In another aspect of the present invention, a water soluble spice and/or herb extract rich in antioxidant phytochemicals was provided for functional food, medical food and cosmecutical applications.

In another aspect of the present invention a stable composition of spice/herbs phytonutrients having a minimum of about 12 month's shelf life for functional food/beverage or medicinal food/beverage applications and also for nutraceutical/cosmecutical applications have been developed.

In another aspect of the present invention a method for producing completely water soluble spice/herb phytonutrient extracts capable of triggering a beneficial pharmacological effect such as antioxidant, anti-inflammatory, blood-sugar management, lipid profile management and or digestive properties is developed depending on the spice/herb used.

In another aspect of the present invention a unique process for producing biologically active water soluble spice extracts suitable for consumption or impregnation in food and beverages without having the problem of taste, aroma, stability or aqueous solubility is developed.

Advantageously yet another aspect of the present invention deals with the development of a formulation for spice/herb antioxidants in ready to use powder or liquid form without any problem of settlement, precipitation, colour change, odour change etc. during storage. A methodology is developed whereby the phytonutrients of spices and herbs can be conveniently delivered for betterment of health, as a beverage or diary food product or as dietary supplement without the problem of taste/aroma issue which normally prevents the consumption of spices and herbs, unlike the fruit and vegetables. Further an organic quality spice/herb phytonutrient extracts for beverage/diary applications is developed. The spice/herb phytonutrients are provided at convenient dosage suitable for triggering beneficial physiological response such as antioxidant status of blood serum, reduction of oxidative stress, reduction of inflammatory markers, enhancement in digestion, ulcer curative property, gastrointestinal health, blood sugar management potential, or hypolipidemic effects, or diuretic as seen from the animal study data and in vitro assays. A beverage/diary ingredient of spices/herbs is produced which is capable of providing 1000 to 5000 ORAC value when consume a serving of food/beverage containing 250 to 500 mg spice extract. Further a fully water soluble spice/herb phytonutrients is provided which is capable of fortifying the nutritional value of other food/beverage products such as fruit juices, milk shakes, etc. without taste/aroma issue. A stable form of spice/herb phytonutrients such as antioxidants to produce antioxidant rich bottled drinking water has been developed. For example, cumin-water or ginger water capable of providing 1000 to 3000 ORAC per a 1 L bottle of water.

In another aspect of the present invention the phytonutrient extracts produced by the present invention have been subjected to human clinical studies to evaluate the in vivo activity of the extracts. For this healthy adult human volunteers aged between 25 and 45 years, who were working in companies, were selected for the clinical studies. Generally, subjects having history of gastrointestinal problems, gallbladder issues, diabetes, hyperlipidaemia etc. or involved in any other medication of health supplements were excluded from the study. Subjects were instructed to maintain their dietary and exercise practices during participation without any major change in their life style. The study was carried out in accordance with the clinical research guidelines established by the basic principles defined in the Scheduled Y, ICH GCP, Indian GCP and ICMR guidelines. Protocol of each study was approved by the institutional ethical committee and written consent from all individuals was obtained before the study. Eligible subjects were assigned a three-digit, unique randomization code. Data on demographic characteristics, medical history, anthropometric measurements (body weight, height, and BMI) were also recorded. Haematological and biochemical parameters, blood sugar and blood pressure of the subjects were analysed to confirm the health state of the subjects.

All the results indicate the phytonutrient extracts of the present invention to be stable, water soluble, without aroma and pungent smell and having very high pharmacological effects.

All specific materials and methods described below, in whole or in part, fall within the scope of the invention. These specific compositions, materials, and methods are not intended to limit the invention, but merely to illustrate specific embodiments falling within the scope of the invention. One skilled in the art may develop equivalent materials, and methods without the exercise of inventive capacity and without departing from the scope of the invention. It will be understood that many variations can be made in the procedures herein described while still remaining within the bounds of the invention. It is the intention of the inventors that such variations are included within the scope of the invention.

Exemplary Embodiments

Embodiment A is a process for the preparation of de-flavoured and de-aromatised food and beverage additives rich in health beneficial bioactive phytonutrients from spices and/or herbs suitable for the impregnation at sufficiently high concentrations per serving to trigger a health beneficial pharmacological effect, said process comprises the steps of mechanically reducing the particle size of the spice and/or herb by a) mechanically reducing the particle size of the spice and/or herb
b) subjecting the product obtained from step (a) to a solvent extraction process
c) filtering the extract to separate the solvent extract and residue
d) concentration of the solvent extract from step (c) to obtain phytonutrient rich extract
e) cooling, settling and filtering the extract obtained from step (d)
f) Blending, homogenizing and filtering the concentrated extract obtained from step (e) with additive and/or natural excipients.
g) Spray drying the blended and filtered composition obtained from step (f)

Embodiment B is a process of embodiment A (step a) wherein the spice and/or herbs are mechanically reduced in particle size by cutting, flaking and/or powdering to a particle size of less than 5 mm, most preferably 1±0.5 mm.

Embodiment C is a process of embodiment A wherein the product obtained from step (a) is optionally subjected to steam distillation or supercritical fluid extraction, prior to extraction step (b)

Embodiment D is a process of embodiment A wherein the extraction step of (b) is optionally a selective solvent extraction, employing water or an organic solvent such as lower aliphatic alcohols, lower aliphatic ketones, and/or their mixtures either alone or in combination with water, depending on the nature of the spice and its phytonutrient content Embodiment E is a process of embodiment A (step b) wherein the solvent for extraction consist of either acetone or ethanol/water mixture at various proportions preferably in the range from about 10:90 to 90:10 v/v or pure water at elevated temperature 60 to 90° C.

Embodiment F is a process of embodiment A (step b) wherein the powdered spice is optionally subjected to ultra-sonication applied as pulses of 1 to 5 min duration or under the microwave conditions at temperature below 50° C.

Embodiment G is a process of embodiment A wherein the step (d) is carried out by evaporation under reduced pressure or further subjecting the concentrated extract to chromatographic separation employing adsorption or ion-exchange resins and eluting the column with lower alcohols, and acetone either alone or in combination with water at definite pH conditions.

Embodiment H is a process of embodiment A wherein the evaporation of solvent in step (d) is slow evaporation using a forced circulation evaporation or spinning cone column evaporation at a rate suitable for the capacity of the evaporator, at a temperature range of 35 to 60° C., preferably at 45 to 50° C., most preferably at 40 to 45° C.

Embodiment I is a process of embodiment A step (d) wherein the concentrated extract has ethanol in the range of about 2000 to about 100 ppm and acetone in a range of about 50 to about 25 ppm.

Embodiment J is a process of embodiment A Step (d) wherein the extract after solvent evaporation has a total dissolved solid (TDS) content of about 15% to about 35% more preferably to about 20% to about 25%.

Embodiment K is a process of embodiment A step (e) wherein the cooling of extract is carried out at a temperature of about 15° C. to ±2° C. for about 3 to about 6 hours, more preferably about 2 to about 4 hours.

Embodiment L is a process of embodiment A wherein the concentrated and cooled extract obtained from step (e) is filtered through a cloth filter having a pore size of about 275 to about 320 microns and further blended as claimed in step (f) and again filtered using above filter cloth.

Embodiment M is a process of embodiment A step (e) wherein the concentrated extract contains phytonutrients such as polyphenols including, but not limited to flavanols, flavonoids, flavanones, anthocyanins, procyandins, stilbenes, etc and volatile oils, terepenoids, alkaloids, fatty acids, fatty alcohols, saponins, carotenoids and chlorophylls.

Embodiment N is a process of embodiment A step (f) wherein the blending of the concentrated extract obtained from step (e) is carried out with suitable natural excipients selected from starch and its modified forms, cellulose and its modified forms, sugar and its food grade derivatives, glucose, fructose, lactose, citric acid, gum acacia, cyclodextrins etc. which are food grade and completely water soluble, to a total dissolved solid (TDS) content of about 4 to about 20%.

Embodiment O is a process of embodiment A wherein the extract obtained from step (e) is blended with 5 to 30% w/w of water soluble additives, 1 to 3% w/w of carbohydrates selected from glucose syrup or cone syrup or sorbitol and 0.5 to 1% w/w of sugar ester.

Embodiment P is a process of embodiment A Step (f) wherein the extract and the additives are homogenized at a pressure of about 250 to 1000 bar, more preferably at a pressure of about 300 to 600 bar in single or multiple stages, depending upon the spice extract.

Embodiment Q is a process of embodiment A step (g) wherein the blended extract of step (f) are spray dried and/or freeze dried and/or microwaved.

Embodiment R is a process of embodiment A wherein the dried powdered extract of step (g) contains to about 1 to 40% of phytonutrient concentration comprising polyphenol content as Gallic acid equivalent, about 0.1 to about 1.0% volatile oil content, about 5 to about 20% proteins, about 20 to about 40% carbohydrates and about 1 to about 10% dietary fibre per 100 g of the spice extract powder.

Embodiment S is a formulation comprising spice and/or herbs phytonutrients produced according to claim 1 which are water soluble with no unfavourable flavour characteristics, capable of impregnating in food, beverages, plain drinking water, medicines and cosmetics such as, but not limited to, dairy products, energy drinks, beverage sachets, ready to use powder drinks, juices, cookies, breakfast cereals, smoothies and snacks for making them healthy and to trigger a healthy pharmacological effect upon its continuous consumption; wherein the said formulation contains 250 to 500 mg of the spice extract having an approximate composition of about 1 to about 40% bioactive antioxidant molecules such as Gallic acid equivalent polyphenol content, about 5 to about 20% proteins, about 20 to about 40% carbohydrates and about 1 to about 10% dietary fibre per 100 g of natural extractives of spice and has an oxygen radical absorbance capacity of about 1000 to 5000.

Embodiment T is a method of improving health and maintaining biological activities such as antioxidant, anti-inflammatory, blood-sugar management, lipid profile management and or digestive properties wherein the food and/or beverage containing about 250 to about 500 mg of the blended composition is provided daily for about 15 days or more depending on the spice/herb used.

EXAMPLES

Example 1

Ethanol/Water Extraction of Cumin Seeds (*Cuminum cyminum*)

Dried cumin seeds (100 Kg; with polyphenol content 0.6% Gallic acid equivalent (GAE)) were crushed and flaked to particles of 0.5±0.2 mm, and charged to an extraction vessel fitted with an agitator, steam jacket, temperature probe, and vapour line. A mixture of ethanol and water, in the ratio 70:30 v/v was added into the extraction vessel. The extract containing micelle was filtered and stored in a separate tank with regular intervals of time (2 h). The extraction was continued for 10 h and the whole extract micelle collected in a vessel. The extract containing micelle was then evaporated under vacuum (700 to 725 mm of Hg) to obtain 200 L free flowing dark brown cumin flavoured liquid. The dark brown cumin flavoured liquid thus obtained was then allowed to settle for 4 h at 18° C. This is filtered through a 300 micron filters cloth under pressure 1 to 1.8 kg/cm$^2$. The clear liquid was emulsified with sugar syrup and gum acacia, thereafter homogenized at 300 bar pressure at 35° C. and spray dried.

Results: The powder obtained by the above process was found to be instantly water soluble with faint characteristic taste and aroma of cumin seeds and found to contain the phytochemicals of cumin such as polyphenols (7.25% Gallic acid equivalent), lipids (18%), volatile oil (1.1%), carbohydrates (53.3%), and proteins (16%). The residual solvents in the powder was found to 48 ppm of ethanol when analysed by a USP <467> General Chapter, Head space method using GC-FID.

The above extraction process was also performed with acetone/water as solvent.

Results: The powder obtained by the above process was found to be instantly water soluble with faint characteristic taste and aroma of cumin seeds and found to contain the phytochemicals of cumin such as polyphenols (8.28% Gallic acid equivalent), lipids (16.8%), volatile oil (0.9%), carbohydrates (53%), and proteins (15.4%). The residual solvents in the powder was found to be 22 ppm of acetone when analysed by a USP <467> General Chapter, Head space method using GC-FID.

The present procedure can be used for other spices and herbs including, but not limited to Coriander, Clove, Fennel, Caraway, Cardamom, Tribulus, Gymnema, Fenugreek, Cocoa, etc. and herbs like Tribulus, Moringa, Emblica, Aswagandha etc.

Example 2

Ethanol/Water Extraction of De-Oiled Cumin Seeds (*Cuminum cyminum*)

100 Kg of dried cumin seeds were flaked (0.5±0.2 mm particles). Flaked dried cumin seeds were introduced into the steam distillation unit connected to the steam generator at the bottom and condenser at the top to cool and the oil vapours into liquid form and hence to collect in the collection vessel, which is kept under vacuum. The essential oils thus obtained were volatilized with steam at temperature 100° C. for 5 to 10 hours. The oil collected in the collection vessel above the water was collected and separated using separating funnel. The oil thus collected is dried over anhydrous sodium sulphate to get the pure essential oil of Cumin. The steam pressure, distillation time and the final yield of oil were adjusted to get the spent Cumin seeds after distillation suitable for further non-volatile phytonutrient extraction. In this case, 3 Kg pressure steam was employed for 6 h to collect 2.2 Kg of oil. After the distillation, the extraction procedure as described in Example 1 was carried out to get water soluble cumin seeds extract powder with no characteristic aroma.

Results: The extract was found to contain polyphenol (5.8% GAE) with instant water solubility and faint characteristic taste of cumin seeds.

Supercritical Extraction for De-oiling Process

The supercritical carbon dioxide (SCFE-$CO_2$) extraction was carried out using supercritical fluid extractor with CO2 cycle system. The extractor vessel with 3×24 Litre capacities was loaded with 10 kg powdered material of spices like cumin, coriander, clove etc. Food grade liquid $CO_2$ was delivered to extraction vessel using high pressure pump. Extraction pressure was varied from 100-180 bars and temperature 40° C. The pressure in the extraction vessel was controlled by back pressure regulator. Heat exchangers were provided in system to maintain temperature in the extractor and separator vessel. Extract was collected every 20 min and 60 min taken for complete extraction of one batch. Then collected the Extract/oil and filtered through 125 micron cloth.

Example 3

Water Extraction of De-Oiled Cumin Seeds
(*Cuminum cyminum*)

Dried cumin seeds (100 Kg; with polyphenol content 0.6% Gallic acid equivalent) were crushed and flaked to particles of 0.5±0.2 mm. This was introduced to an extraction vessel fitted with an agitator, steam jacket, temperature probe, and vapour line. Purified water (3 to 5 times excess) was added into the extraction vessel and extracted for 3 h with agitation. The extract containing micelle was filtered and stored in a separate tank with regular intervals of time (3 h). The extraction was continued for 10 h and the whole extract micelle collected in a vessel. The extract micelle thus obtained was then evaporated under vacuum (700 to 725 mm of Hg) to obtain 200 L free flowing dark brown cumin flavoured liquid. The dark brown cumin flavoured liquid thus obtained was then allowed to settle for 4 h at 18° C. It is then filtered through a 300 micron filter cloth under pressure of about 1.1 to 1.8 Kg/cm². The clear liquid thus obtained was emulsified with sugar syrup and gum acacia. The mixture was homogenized at 300 bar pressure at 35° C. and spray dried.

Results: The powder thus obtained was found to be instantly water soluble with faint characteristic taste and aroma of cumin seeds and found to contain the phytochemicals of cumin such as polyphenols (5.25% Gallic acid equivalent), lipids (17.2%), volatile oil (0.93%), carbohydrates (57.3%), and proteins (15.1%).

The present procedure can be used for other spices and herbs including, but not limited to Coriander, Clove, Fennel, Caraway, Cardamom, Tribulus, Gymnema, Fenugreek, Cocoa, etc.

Example 4

Ethanol/Water Extraction of Oil-Rich Spices. e.g.:
Clove Buds (*Szygium aromaticum*)

Dried Clove buds (100 Kg; with polyphenol content 8.2% Gallic acid equivalent) were crushed and flaked to particles of 0.5±0.2 mm. The crushed and flaked buds were charged to a supercritical extractor and extracted using carbon dioxide at 10 to 16 mPa pressure and 40° C. The essential oil obtained (Product A) is removed. The spent obtained after oil extraction (80 kg) was charged into an extraction vessel fitted with an agitator, steam jacket, temperature probe, and vapour line. A mixture of hexane/acetone (80:20 v/v) was further added (3 to 5 time's excess) into the extraction vessel and extracted for 3 h with agitation. The extract containing micelle was filtered and stored in a separate tank with regular intervals of time (3 h). The extraction was continued for 10 h and the whole extract micelle collected in a vessel. The extract containing micelle thus stored was then evaporated under vacuum (700 to 725 mm of Hg) to obtain 200 L free flowing dark brown clove flavoured liquid. It was further concentrated to get 12 Kg of dark brown pasty mass called oleoresin (product B).

The spent after oleoresin extraction is heated to 60 to 80° C. with agitation to remove all the trapped solvents to less than 25 ppm level. A mixture of ethanol/water was then pumped into the vessel as detailed in example 1. The clear ethanol/water concentrate obtained after ethanol evaporation and concentration was further mixed with 40 g of essential oil from product A and 60 g of oleoresin from product B and further with gum acacia (2.4 kg), sorbitol 100 g and water 70 L. Then homogenized at 400 bar pressure and spray dried to obtain an off-white coloured powder.

Results: The product A obtained was about (13.2 Kg) with 87% eugenol. The off-white powder obtained was found to have a phytochemicals of clove such as polyphenols (35.25% Gallic acid equivalent), lipids (7%), volatile oil (0.91%), eugenol (0.76%) carbohydrates (42.25%), and proteins (10%). The residual solvents in the powder was found to 52 ppm of ethanol when analysed by a USP <467> General Chapter, Head space method using GC-FID.

The present procedure can be used for other spices and herbs including, but not limited to Cinnamon, Ginger, Allspice, Cardamom and Nutmeg etc.

Example 5

Estimation of Polyphenol Content

Polyphenol content was estimated with Folin-Ciocaltue method as Gallic acid equivalent (Singleton V. L and Rossi J. A. American Journal of Ecology and Viticulture, 1965, 16, pp. 144-158).

Results: Polyphenol content of various spice extracts prepared by the protocol of extraction mentioned in examples 1 to 4 are shown in (FIG. 1).

Example 6

(1) In Vitro Antioxidant Effects of Water-Soluble
Spice Phytonutrient Extract (Cumin, Ginger,
Coriander and Clove)

(i) Superoxide Radical Anion Scavenging Activity

McCord and Fridovich, (1969), measure super oxide radical anion scavenging activity. Briefly, 1 mg/mL spice extract stock solution was prepared in distilled water. The reaction mixture contained 200 μL KCN [dissolved in EDTA (6 mM)], 50 μL riboflavin (0.12 mM), 100 μL NBT (1.5 mM) and various concentrations (1-10 μg/mL) of the extract and add Phosphate buffer made up to 3 mL. The tubes containing the reaction mixture were uniformly illuminated with an incandescent lamp for 15 minutes. The absorbance was measured at 530 nm before and after the illumination. Percent inhibition of superoxide radical was calculated using the equation:

$$\% \text{ inhibition} = \frac{(OD \text{ of control} - OD \text{ of test})}{OD \text{ of control}} \times 100$$

Results: $IC_{50}$ values of cumin, ginger, coriander, and clove were found to be 9.33 μg/mL, 30.6 μg/mL, 17.6 μg/mL and 12.5 µg/mL respectively; while Vitamin C produced an IC$_{50}$ values 1900 µg/mL (FIG. 2).

(ii) Hydroxyl Radical Scavenging Activity

Hydroxyl radical scavenging activity of the extract was measured by following the method of Elizabeth and Rao, (1990). Briefly, 1 mg/mL spice extract stock solution was prepared in distilled water and mixed with the reaction mixture containing deoxyribose (2.8 mM), ferric chloride (0.1 mM) EDTA (0.1 mM), H$_2$O$_2$ (1 mM), ascorbate (0.1 mM), and KH$_2$PO$_4$—KOH (20 mM, pH 7.4) at various concentrations (1-10 µg/mL) to a total volume of 1 mL and incubated for 1 hr at 37° C. Absorbance of each solution was measured at 530 nm using a UV/VIS spectrophotometer against the distilled water as reference. From the absorbance of the control and test solution, percentage inhibition was calculated.

$$\% \text{ inhibition} = \frac{(\text{Absorbance of control} - \text{Absorbance of test})}{\text{Absorbance of control}} \times 100$$

Results: IC$_{50}$ values of cumin, ginger, coriander, and clove were found to be 275 µg/mL, 159 µg/mL, 296 µg/mL and 185 µg/mL respectively; while Vitamin C produced an IC$_{50}$ values 1550 µg/mL (FIG. 2).

(iii) Lipid Peroxidation Assay

The level of lipid peroxidation was measured by the method of Ohkawa et al (1979). Briefly, 1 mg/mL spice extract stock solution was prepared in distilled water. Various concentrations (1-10 µg/mL) of extract were incubated with 0.1 mL rat liver homogenate (25%) containing 30 mM KCl, Tris-HCl buffer (0.04 M, pH 7.0), ascorbic acid (0.06 mM) and ferrous ion (0.16 mM) in a total volume 0.5 mL for 1 hr. After incubation, 0.4 mL of reaction mixture was treated with 0.2 mL SDS (8.1%), 1.5 mL TBA (0.8%) and 1.5 mL acetic acid (20%, pH 3.5) distilled water were kept for 1 hr in a boiling water bath at 100° C. After 1 h, the reaction mixture was removed from the water bath, cooled and added 5 ml of pyridine:butanol (15:1 ratio), mixed thoroughly and centrifuged at 3000 rpm for 10 mM. Absorbance of the clear supernatant was measured at 532 nm against pyridine:butanol. Percent inhibition of lipid peroxidation was calculated using the equation:

$$\% \text{ inhibition} = \frac{(\text{Absorbance of control} - \text{Absorbance of test})}{\text{Absorbance of control}} \times 100$$

Results: IC$_{50}$ values of cumin, ginger, coriander, and clove were found to be 99 µg/mL, 102 µg/mL, 125 µg/mL and 75 µg/mL respectively; while Vitamin C produced an IC$_{50}$ values 375 µg/mL (FIG. 2).

(iv) CAP-e (Cellular Antioxidant Protection—Erythrocyte Model) Test

CAP-e assay was performed as per the protocol reference NIS/CAPe/AAPH/20090803 of NIS Lab, 1437 Esplanade, Klamath Falls, Oreg. 97601, www.NISLABS.com. The CAP-e value is in Gallic Acid Equivalent (GAE) units. Briefly, 0.5 g of each water-soluble spice phytonutrient extracts was mixed with 5 mL 0.9% saline at physiological pH and centrifuged at 2400 rpm for 10 minutes. The supernatant of the products was harvested and then filtered for use in the CAP-e assay. Serial dilutions are prepared from each filtered supernatant in 0.9% saline. Red blood cells are treated in duplicate with serial dilutions of a test product. Samples of untreated red blood cells (negative controls) and samples of red blood cells treated with oxidizing agent but not with an antioxidant-containing test product (positive controls) are prepared in hexaplicate. The antioxidants not able to enter the cells are removed by centrifugation and aspiration of supernatant above the cell pellet. The cells are exposed to oxidative damage by addition of the peroxyl free-radical generator AAPH (2,2'-azobis-2-methyl-propanimidamide, dihydrochloride). Using the indicator dye DCF-DA (2',7'-dichlorfluorescein-diacetate), which becomes fluorescent; because of oxidative damage, the degree of antioxidant damage is recorded by measuring the fluorescence intensity of each test sample. The inhibition of oxidative damage is calculated as the reduced fluorescence intensity of product-treated cells, compared to cells treated only with the oxidizing agent. The CAP-e value reflects the IC$_{50}$ dose of the test products. This is then compared to the IC$_{50}$ dose of the known antioxidant Gallic Acid.

Results: IC$_{50}$ values of cumin, ginger, coriander, and clove were found to be 71, 63, 76 and 85 mg Gallic acid equivalent respectively (FIG. 2).

(v) ORAC (Oxygen Radical Absorbance Capacity) Test:

Oxygen radical absorbance capacity (ORAC) assay has been received attention as a benchmark analysis for antioxidant efficacy due to its relevance to in vivo efficacy. The measurements were made as per the method of Wu et al, 2004. Oxygen radical absorbing capacity (ORAC) was measured on the basis of the capacity of the extract to stabilize the fluorescence signal of a fluorescence probe (fluorescein sodium) over the time which in turn directly related to the capacity of the extract to neutralize the peroxy radicals generated from the decomposition of 2,2'-azobis(2-amidino-propane)dihydrochloride (AAPH) and expressed as Trolox equivalents.

Results: IC$_{50}$ values of cumin, ginger, coriander, and clove were found to be 4500 µmol TE/g, 5600 µmol TE/g, 3800 µmol TE/g and 9200 µmol TE/g respectively (FIG. 2).

Example 7

In Vitro Free Radical Scavenging Activity of Water-Soluble Spice Phytonutrient Extracts (Cumin, Ginger, Coriander and Clove)

(i) DPPH (2,2,-diphenyl-1-picryl hydrazyl) Assay 1 mg/mL spice extract stock solution was prepared in distilled water was tested for their scavenging activity against the stable free radical DPPH (2,2-diphenyl-1-picryl hydrazyl) was determined by method of Aquino et al., 2001. Briefly, various concentrations of the extract were added to 1 mL of freshly prepared DPPH solution in methanol. The reaction mixture was made up to 2 mL with methanol; incubated for 20 minutes; read at 515 nm against methanol as reference. The percentage inhibition was calculated and concentration needed for 50% inhibition was found out.

$$\% \text{ inhibition} = \frac{(\text{Absorbance of control} - \text{Absorbance of test})}{\text{Absorbance of control}} \times 100$$

Result: IC$_{50}$ values of cumin, ginger, coriander, and clove were found to be 20.25 µg/mL, 25 µg/mL, 45 µg/mL and 6 µg/mL respectively; while Vitamin C produced an IC$_{50}$ values 14 µg/mL (FIG. 3).

(ii) ABTS (2',2-azino-bis-3-ethyl benzthiazoline 6-sulphonic acid) Assay

The antioxidant effect of the spice extracts was studied by their ability to scavenge the free radical ABTS (2',2-azino-bis-3-ethyl benz thiazoline 6-sulphonic acid) by the method determine by Shirwaikar et al., 2006. Briefly, Dissolve ABTS (38.4 mg) in 10 mL distilled water to this added 5.59 mg Ammonium per sulphate taken in brown bottle. Keep ABTS solution at Room temperature for 16 hours, and then store it at 4° C. (if not use). Take 500 µL, ABTS solution and add 50 mL PBS; adjust the OD to 0.7-0.8 against PBS as reference at 734 nm. Take 1 mL ABTS solution with different varies concentration of the extracts (1 mg/mL spice extract stock solution was prepared in distilled water) and made up to 2 mL with PBS. Keep the sample at room temperature for 6 minutes. The absorbance was measured at 734 nm. The results were calculated from the slopes of reaction curves obtained by plotting the absorbance Vs time.

$$\% \text{ inhibition} = \frac{(\text{Absorbance of control} - \text{Absorbance of test})}{\text{Absorbance of control}} \times 100$$

Result: $IC_{50}$ values of cumin, ginger, coriander, and clove were found to be 13.37 µg/mL, 28 µg/mL, 14.75 µg/mL and 12.35 µg/mL respectively; while Vitamin C produced an $IC_{50}$ values 2.25 µg/mL (FIG. 3).

(iii) FRAP (Ferric Reducing Ability of Plasma) Assay

The extract was tested for their scavenging activity against the stable free radical FRAP reagent is determined by the method Benzie et al. 1996. Briefly, various concentration of spice extract (1 mg/mL spice extract stock solution was prepared in distilled water) were added to each amber colour eppendrof and to it about 900 µL of FRAP reagent (25 mL acetate buffer+2.5 mL Fe III $T_PT_Z$+2.5 mL $FeCl_3$) was added. The reaction mixture was made up to 1 ml with distilled water, incubated at 37° C. for 15 minutes and the absorbance is read at 595 nm against water as control. The value obtained from a $FeSO_4.7H_2O$ standard graph expressed. The ferric reducing activity of drug concentration is equal to the reducing power $FeSO_4.7H_2O$.

Result: The ferric reducing activity of 30 µg each of cumin, ginger, coriander and clove were equivalent to the reducing power 637.5 µmol/L of $FeSO_4.7H_2O$, 712.5 µmol/L of $FeSO_4.7H_2O$, 512.5 µmol/L of $FeSO_4.7H_2O$, and 635.25 µmol/L of $FeSO_4.7H_2O$ compared to the control whose concentration of $FeSO_4.7H_2O$ was 1.096 mM (FIG. 3).

Example 8

Preparation of Phytonutrient Extract Fortified Food/Beverages (i) Powdered Drinks Sachet Below mixture of ingredients was prepared as a free flowing fine powder and 5 g of the mixture was dissolved in water or milk at 50 to 60° C. to get a ready to drink beverage.

| Ingredients | % Concentration |
|---|---|
| Spice extract powder (Cumin, coriander, ginger, cardamom etc.) | 250 mg |
| Cocoa powder | 4% |
| Chocolate or food flavour | 34% |
| Sugar | 60% |
| Vanilla | 2% |

(ii) Plane Drinking Water Fortified with Spice Phytonutrient Extract

| | |
|---|---|
| Spice extract powder (Cumin, coriander, ginger, cardamom etc.) | 150 mg |
| Water | 250 mL |

(iii) Yoghurt Fortified with Spice Phytonutrient Extract

| | |
|---|---|
| Spice extract powder (Cumin, coriander, ginger, cardamom etc.) | 200 mg |
| Yoghurt | 150 |

(iv) Beverage Fortified with Spice Phytonutrient Extract

| (a) With fruit powder | |
|---|---|
| Cumin extract powder | 150 mg |
| Lemon or mango powder | 5 g |
| Sugar free | 1 g |

Results: The Polyphenol content of the preparation was found to be 9 mg/Glass

| (b) With green tea extract | |
|---|---|
| Cumin extract powder | 150 mg |
| Green tea extracts | 100 mg |

Results: The Polyphenol content of the preparation was found to be 9 mg/Glass

| (c) Sherbet fortified with spice phytonutrient extract | |
|---|---|
| Cumin extract powder | 150 mg |
| Sherbet(In dilute form) | 10 mL |

Results: The Polyphenol content of the preparation was found to be 9 mg/Glass

| (c) Honey fortified with spice phytonutrient extract | |
|---|---|
| Cumin extract powder | 150 mg |
| Honey | 10 g |

Results: The Polyphenol content was found to be 9 mg/Cup

Example 9

Effect of De-Flavoured Cumin Extract Incorporated Potato Chips on the Antioxidant Activity. (In Vitro Assays)

| | |
|---|---|
| Potato chips | 25 g |
| Cumin extract powder | 400 mg |

400 mg Cumin extract powder prepared as explained in example 1, was dissolved in sunflower oil (5 mL) and sprinkle it to the 25 g fried potato chips. Mix well and this was given to five volunteer for sensory evaluation. The sample was first de-oiled and its antioxidant level was check using DPPH, ABTS, & SOD method comparing with plain potato chips.

Result: The antioxidant level of DPPH, ABTS & SOD for plain potato chip is 35 µg/mL, 28.41 µg/mL and 22.3 µg/mL respectively and for cumin added potato chip is 26.5 µg/mL, 22.13 µg/mL & 9.33 µg/mL (FIG. 4). The sensory evaluation states it's having good taste and easily to consume.

Example 10

Pharmacological Studies/Clinical Studies

The animals for experimental model were taken from small breeding station of Amala Cancer Research Centre, Thrissur (Registration No. 149/99/CPCSEA) and Amrita Institute of Medical Science, Kochi (Registration No. 527/02/a/CPCSEA). The animals were kept in air-conditioned room at 22±2° C. and relative humidity 60±5° C. with 12 hours day and light cycle, fed with normal mouse chow, a natural ingredient diet (Sai Feeds, India) and water ad libitum. All animal experiments were performed according to the rules and regulations of the Committee for the Purpose of Control and Supervision of Experiments on Animals (CPCSEA), Government of India.

Animal Studies (i) In Viva Anti-Inflammatory Potential—(Carrageenan Induced Paw Oedema Model) Using De-Flavoured Clove Extract Powder—Water Soluble (Prepared as Explained in Example 3)

Five groups each contained six Male Swiss albino mice (25-30 g) in each group were injected with 25 μL of 1% suspension of carrageenan in 0.1% carboxy methylcellulose (CMC) sub-planetary into right hind paw. Paw volume was measured at various time intervals such as, paw volume before inflammation induction, then for 1, 2, 3, 4, 5 and 24 hours after carrageenan administration using a vernier calliper. Clove extract at doses 25, 50 and 100 mg/kg body weight was administered (orally) 1 hour prior to carrageenan injection. Diclofenac (15 mg/kg) was used as standard reference drug. The percentages of inhibition were calculated according to the following formula.

$$\% \text{ inhibition} = \frac{([VT - Vo]\text{control} - [VT - Vo]\text{treated group})}{VT - \text{control}} \times 100$$

Where, VT—Paw oedema at various time intervals and Vo—Initial paw oedema

Groups and Dosages

| Group 1: | Control injected with carrageenan (25 μL). |
|---|---|
| Group 2: | Administered with 10 mg/ml Diclofenac + 1% carrageenan injection (25 μL). |
| Group 3: | Administered with 25% Clove extract at 100 mg/kg body weight + 1% carrageenan injection (25 μL). |
| Group 4: | Administered with 50% Clove extract 100 mg/kg body weight + 1% carrageenan injection (25 μL). |
| Group 5: | Administered with 100% Clove extract 100 mg/kg body weight + 1% carrageenan injection (25 μL). |

Results: The inflammatory study evaluated the carrageenan-induced paw volume increase, and the effects of de-flavoured Clove extract and reference drug diclofenac. The results of the inhibition caused by Clove extract and diclofenac were, assessed at 1, 2, 3, 4, 5 and 24 hr after the sub plantar injection of carrageenan. Carrageenan produced significant oedema in the mice paws, reaching a maximum at $3^{rd}$ hour. Oral administration of Clove extract the caused dose related reduction in carrageenan induced paw edema volume than that of control. The Clove extract at the doses of 25, 50 and 100 mg/kg body weight exhibited significant (p<0.01) anti-inflammatory activity with 49.23%, 53.34% and 62.84% inhibition respectively at 3rd h after carrageenan administration (FIG. 5). While the standard reference drug diclofenac at dose 50 mg/kg body weight produced a higher inhibition of 56.70%.

(iv) Antidiabetic Potential—Estimated by Glucose Tolerance Test.

Wistar rats (150-200 g) were divided into 5 groups each containing 6 animals.

| Group 1: | Kept as normal (without any treatment) |
|---|---|
| Group 2: | Control were given distilled water |
| Group 3: | Administered with Cinnamon at a dose of 250 mg/kg body weight |
| Group 4: | Administered with Clove at a dose of 250 mg/kg body weight |
| Group 5: | Administered with Cumin at a dose of 250 mg/kg body weight |

Glucose at 5 g/kg body weight was given orally to all the groups except normal group, one hour after drug administration
Blood samples were collected from tail vein just prior to drug administration and 30 min, 1, 1½, 2, 3, 4 and 6 hr after the glucose loading and blood glucose levels were measured using a blood glucose meter (M/s Bayer & Contour, Japan)

Results: Administration of glucose (5 g/kg) in control group increased the serum glucose level from 103.79 to 204.36 mg/dL after 1 hour and then reduced gradually from 1½ hour to $6^{th}$ hour (129.68±9.13 mg/dL). When Cinnamon, Clove & Cumin extract was administered at 250 mg/kg body weight of animals, the relative enhancement in the blood glucose level after 1 hour of consumption was reduced significantly from the control group, to a level of 153.6±4.41 mg/dL, 168.57±5.93 mg/dL and 175.6±7.32 mg/dL respectively for cinnamon, clove and cumin extracts. The blood glucose level was subsequently reduced gradually from 1½ hour to $6^{th}$ hour Cinnamon (105.48±7.29 mg/dL), Clove (112.54±3.84 mg/dL) and Cumin (120.38±2.35 mg/dL) when compared to control. The reduction in serum glucose level by different spice was found to be Cinnamon>Clove>Cumin (FIG. 6).

(v) Hypolipidemic Activity in Fat Diet Induced Obese Models.

The effects of de-flavoured clove extract on plasma lipid levels in high cholesterol-fed nine-week-old male Sprague-Dawley rats were studied. 9 week old Sprague-Dawley rats were divided into 4 groups each containing 6 animals.

| Group 1: | Fed on a normal diet (without any treatment) |
|---|---|
| Group 2: | Fed on high cholesterol diet (HCD) containing 1% cholesterol and 15% fat (HCD) without Clove |
| Group 3: | Fed with HCD along with 100 mg/kg body weight of clove |
| Group 4: | Fed with HCD along with 250 mg/kg body weight of clove |

The feeding time for all the groups was for a period of 4 weeks
Blood was taken from the tail vein before and at the end of each week during the feeding period, and the plasma cholesterol level was measured
At the end of the experiment, each animal was anesthetized with ethyl ether, a blood sample was taken from the abdominal vein, and the liver was removed and stored at –80° C. until analysis Results: The total cholesterol concentration in plasma was markedly increased throughout the experimental period by ingestion of the HCD. Plasma cholesterol level was significantly higher in the HCD without clove extract group (220 mg/dL) than the normal diet group (98 mg/dL) (p<0.01). In contrast, this increase was strikingly inhibited by clove supplementation (105 mg/dL). The plasma total cholesterol levels of clove groups were somewhat closer to the normal diet group (p<0.01). A significant difference between the normal diet group and the HCD without clove group was seen in free cholesterol but not in the other plasma lipid levels (FIG. 7).

Human Clinical Studies (i) Effect of Water Soluble and De-Flavoured Clove Extract (Prepared as Explained in Example 3) was Impregnated in Food Consumption on Oxidative Stress of Healthy Human Volunteer.

200 mg/serving of de-flavoured clove extract was impregnated in various foods products such as honey, mango juice, yogurt, and consumed at 200 mg/serving/day level for 30 days. Each group contain 5 volunteer each. Blood of the subjects on initial day and on $30^{th}$ day was withdrawn and the plasma was separated by centrifugation. The antioxidant status of the plasma was analysed by estimating SOD, glutathione (GSH) and lipid peroxidation levels.

(a) Estimation of Super Oxide Dismutase (SOD) Activity.

SOD activity was determined according to the method of McCord and Fridovich (1969) and expressed as IU/Hb. Briefly, 100 µL Blood sample+0.9 mL cold water (4° C.). Then add 0.25 mL of chloroform and 0.5 mL ethanol with vigorous mixing. Then centrifuge under cold condition 1800 rpm for 60 minutes. 100 µL supernatant is mixed with 200 µL EDTA and 100 µL NBT and with SOD buffer made up to 3 mL. Riboflavin (50 µL) is added just before reading. Absorbance was read at 560 nm against distilled water as reference. Calculation by the formula, SOD Value=1/y, where y is $$y = \frac{\frac{(100 \times 50)}{\% \text{ inhibition}} \times Hb}{1750};$$

$$\% \text{ inhibition} = \frac{(OD \text{ of control} - OD \text{ of test})}{OD \text{ of control}} \times 100$$

Result: Clove extract (200 mg/serving/day) impregnated food and beverages consumption for 30 days showed a significant elevation of SOD levels from the baseline value (initial day) to the $30^{th}$ day; 1.102±0.05 U/mL, 1.126±0.07 U/mL & 1.144±0.24 U/mL for mango juice, yogurt & honey respectively. Superoxide dismutase level showed an average of 66% increase when compared to the initial values (FIG. 8A).

(b) Estimation of Reduced Glutathione (GSH)

Reduced glutathione was determined according to the method of Moron et al., (1979) with minor modifications. Briefly, 100 µL bloods+125 µL of 25% Trichloroacetic acid (TCA) keep in cool condition for 5 minutes. 0.6 mL of 5% TCA is added to it and centrifuges it for 10 minutes at 2000 rpm. 100 µL of sample+334 µL GSH buffer and 667 µL DTNB (added prior before taking the reading). Absorbance at 412 nm with reference distilled water. Obtained absorbance is plotted against the standard graph of glutathione and expressed as nmoles/mg Hb Result: The effect of various food beverages showed a significant elevation from the initial day to the $30^{th}$ day such as 44.2±11.56 nmoles/mg Hb, 49.2±10.89 nmoles/mg Hb & 54.2±18 nmoles/mg Hb after consumption of mango juice, yogurt & honey (200 mg clove extract/serving/day) respectively. Glutathione level showed 108% when compared to the initial values (FIG. 8B).

(c) Estimation of Malondialdehyde for Serum (MDA)

MDA was determined by the method based on Vali Pasha and Sadasivudu, Neuroscience letters, 46(1984)209-214. Briefly, 1 mL serum is added to 1 mL of 40% TCA followed by the addition of 2 mL 0.67% TBA. The mixture was kept for 10 minutes in boiling water. Then cool it; centrifuge for 10 minutes at 6000 rpm. Absorbance read at 530 nm against distilled water as reference. Calculate E=KCL and expressed as nmoles/dL.

$$C = \frac{E}{K * L} \text{nmoles/dL}$$

Where K=Molar Extinction Coefficient=1.5×10$^5$; E=Absorbance; C=Concentration in moles/L; L=Length of cuvette used=1 cm Result: The effect of various food beverages showed a significant reduction from the initial day to the $30^{th}$ day such as 56.77±15.5 nmoles/dL, 50.8±4.9 nmoles/dL & 49.54±3.72 nmoles/dL of mango juice, yogurt & honey (200 mg clove extract/serving/day) respectively. The elevated antioxidant enzymes have also found to contribute to a significant inhibition in plasma lipid peroxidation (83%) (FIG. 8C).

The antioxidant effect from the various food/beverage was found to be in the order honey>yogurt>juice with the relative average difference of ±15%, indicating their effectiveness as dietary ingredient.

(ii) Effect of Drinking Plain Water Containing De-Flavoured Clove Extract (Prepared as Explained in Example 3) at 250 mg/150 mL/Day for 15 Days Five volunteer where given 200 mg/serving of de-flavoured clove extract was impregnated plain water and consumed at 200 mg/serving/day level for 15 days. Blood of the subjects on initial day and on $15^{th}$ day was withdrawn and the plasma was separated by centrifugation. The antioxidant status of the plasma was analysed by estimating SOD and glutathione (GSH) levels as per above procedure explained.

Results: The results demonstrated a significant reduction in oxidative stress as evident from the elevation in the primary antioxidant defense enzymes SOD (1.02±0.12 U/mL) and GSH (44.5±2.3 nmoles/mg Hb) as compared to the initial values. Showed that antioxidant level increase as the consumption of clove extract in plain water daily (FIGS. 9 A & B).

(iii) Effect of Consumption of De-Flavoured Cinnamon Extract (Prepared as Explained in Example 4) in Breakfast Cereal for 20 Days.

Six volunteer was given 30 g breakfast cereal and add 200 mL pasteurized milk (hot/cold) and pinch of sugar for taste. Mix well and serve it for breakfast for 20 days. The initial and final day blood is withdrawn. The oxidative stress is evaluated by SOD, GSH, MDA (as per procedure explained above). A wash out period was kept for two weeks; the same volunteer was given 500 mg Cinnamon added to 30 g breakfast cereal. The experiment was repeated for 20 days and blood analysis was performed.

Result: The result showed that on the addition of Cinnamon extract in breakfast cereal showed and increased in antioxidant level. A significant the elevation in the primary antioxidant defense enzymes SOD on cereal with cinnamon and plain cereal was 1.21±0.06 U/mL and 0.93±0.05 U/mL respectively after 20 days consumption. Similarly an elevation was also shown in GSH upon the consumption of cereal with cinnamon and plain cereal was 65.6±4.51 nmoles/mg Hb and 52.6±1.95 nmoles/mg Hb respectively as compared to the initial values. Reduction on Lipid peroxidation when cinnamon was added to cereal and plain cereal as such consumed was found to be 149.6±24.44 nmoles/dL and 164.6±30.44 nmoles/dL respectively when compared to the initial values [FIGS. 10 (A, B & C)].

(vi) Effect of Consumption of De-Flavoured Cinnamon Extract (Prepared as Explained in Example 4) in Breakfast Cereal to Check its Glycemix Index Normal (soup with known nutritional profile) - 150 mL
Cinnamon (500 mg) + Kellogg's (30 g) + Pasteurized milk (150 mL)
Breakfast cereal (30 g) + Pasteurized milk (150 mL)
Control given Glucose (50 g)
Six volunteer was volunteered for the experiment and one week wash out period was given to perform the study.
Blood Glucose level was check at intervals of 30 minutes, 1 hour, 1.5 hour & 2 hours was check by glucometer Result: The result showed that there was an increase of blood sugar level at $1^{st}$ hour and significantly a reduction of the blood glucose level at the $2^{nd}$ hour; normal (93±1 mg/dL), cinnamon with cereal (96.5±2.64 mg/dL), cereal alone (100±4.8 mg/dL) as compared to glucose (103.5±10.5 mg/dL) (FIG. 11).

We claim:

1. A process for the preparation of a food or beverage ingredient from a spice and/or herb selected from the group consisting of Coriander, Clove, Fennel, Ginger, Caraway, Nutmeg, Mace, Celery, Cardamom, Cumin, Cinnamon, Amla (Emblica), Moringa (Moringa olifera), Tribulus, Fenugreek, Cocoa, Coffee, Tumeric, Aswagandha, and Gymnema, said process comprising the steps of:
    a) reducing the particle size of the spice and/or herb, to less than 5 millimeters to obtain a product;
    b) deflavoring and dearomatizing the product obtained from step a) by solvent extraction, wherein the solvent includes an organic solvent, or organic solvent and water, and wherein the organic solvent is selected from: lower aliphatic alcohols, lower aliphatic ketones, and/or or a mixture thereof, to provide a mixture of liquid solvent extract and residue;
    c) filtering the liquid solvent extract from the mixture of step b) to separate the liquid solvent extract from the residue;
    d) concentrating the liquid solvent extract from step c) at 40 to 45° C. to obtain a phytonutrient extract including volatile and non-volatile antioxidants;
    e) cooling the phytonutrient extract obtained from step d) at a temperature of approximately 15° C. for about 3 to 6 hours and filtering the phytonutrient extract obtained from step d) to obtain a concentrated liquid filtrate;
    f) protecting the volatile and non-volatile antioxidants in the concentrated liquid filtrate obtained from step (e) by adding protective additives to the concentrated liquid filtrate containing volatile and non-volatile antioxidants and homogenizing at a pressure of about 250 to 1000 bars; and, g) drying the liquid filtrate obtained from step (f).

2. The process of claim 1, wherein the particle size of said spice and/or herbs is mechanically reduced by cutting, flaking and/or powdering to provide a particle size of less than 1.5 mm.

3. The process of claim 1, wherein the spice and/or herb of reduced particle size obtained from step a) is subjected to steam distillation or supercritical fluid extraction, prior to extraction step b).

4. The process of claim 1, wherein in step b) the organic solvent comprises acetone and water, or ethanol and water in a ratio of about 10:90 to 90:10 v/v, respectively.

5. The process of claim 1, wherein at step b) the product obtained from step a) is subjected to ultra-sonication pulses at a duration of at least one of 1 to 5 min, or to microwave conditions, at a temperature below 50° C.

6. The process of claim 1, wherein step d) is carried out by evaporation under reduced pressure or subjecting the liquid solvent extract of step c) to adsorption or ion-exchange chromatography with a stationary phase comprising a resin including divinyl benzene cross-linked polystyrene or polyamide and using lower alcohols and acetone either alone or in combination with water as eluents.

7. The process of claim 6, wherein the concentration of the liquid solvent in step d) is concentrated with forced circulation evaporation or spinning cone column evaporation at a rate suitable for the capacity of the evaporator, at a temperature range of 35 to 60° C.

8. The process of claim 1, wherein at step d) the concentrated liquid extract contains ethanol in the range of about 100 parts per million (ppm) to about 2000 ppm, and acetone in a range of about 25 ppm to about 50 ppm.

9. The process of claim 1, wherein at step d) the extract after solvent evaporation has a total dissolved solid (TDS) content of about 15% to about 35%.

10. The process of claim 1, wherein filtering the concentrated and cooled phytonutrient extract in step e) includes filtering the phytonutrient extract through a cloth filter having a pore size of about 275 to about 320.

11. The process of claim 1, wherein at step d) said phytonutrient extract comprises phytonutrients including polyphenols, said polyphenols including, flavanols, flavonoids, flavanones, anthocyanins, procyandins, stilbenes, said phytonutrients further including volatile oils, terepenoids, alkaloids, fatty acids, fatty alcohols, saponins, carotenoids and chlorophylls.

12. The process of claim 1, wherein the protective additives are excipients selected from the group consisting of starch and its modified forms, cellulose and its modified forms, sugar and its food grade derivatives, glucose, fructose, lactose, citric acid, gum acacia and cyclodextrins.

13. The process of claim 1, wherein the liquid filtrate obtained from step e) is blended with 5 to 30% w/w of water soluble additives, 1 to 3% w/w of carbohydrates selected from glucose syrup or cone syrup or sorbitol, and 0.5 to 1% w/w of sugar ester.

14. The process of claim 1, wherein step f) additionally comprises: homogenizing the liquid filtrate at a pressure of about 250 to 1000 bar.

15. The process of claim 1, wherein at step g) the drying includes one or more of spray drying, freeze drying, or, microwave drying.

16. The process of claim 1, wherein drying the liquid filtrate includes drying the liquid filtrate to result in a powder of about 1 to 40% of phytonutrient concentration comprising polyphenol content as Gallic acid equivalent, about 0.1 to about 1.0% volatile oil content, about 5 to about 20% proteins, about 20 to about 40% carbohydrates, and about 1 to about 10% dietary fiber per 100 g of the spice extract powder.

17. The process of claim 1, wherein the additives have encapsulating and solubility properties.

* * * * *